United States Patent [19]

Koszalka et al.

[11] Patent Number: 5,185,437
[45] Date of Patent: Feb. 9, 1993

[54] THERAPEUTIC NUCLEOSIDES

[75] Inventors: George W. Koszalka, Chapel Hill; Charlene L. Burns, Durham; Thomas A. Krenitsky, Chapel Hill; Janet L. Rideout, Raleigh, all of N.C.

[73] Assignee: Burroughs Wellcome Co., Research Triangle Park, N.C.

[21] Appl. No.: 753,060

[22] Filed: Aug. 31, 1991

Related U.S. Application Data

[60] Division of Ser. No. 417,989, Oct. 6, 1989, Pat. No. 5,068,320, which is a continuation-in-part of Ser. No. 179,435, Apr. 8, 1988, abandoned.

[30] Foreign Application Priority Data

Apr. 9, 1987 [GB] United Kingdom ............... 8708512
May 29, 1987 [GB] United Kingdom ............... 8712691
Sep. 30, 1987 [GB] United Kingdom ............... 8723013

[51] Int. Cl.$^5$ ............................ C07H 19/173
[52] U.S. Cl. ................................. 536/24
[58] Field of Search ............. 514/45, 46; 536/24, 536/26

[56] References Cited

U.S. PATENT DOCUMENTS

4,724,232 2/1988 Rideout et al. .................. 514/50
5,068,320 11/1991 Koszalka et al. ................. 536/24

FOREIGN PATENT DOCUMENTS

0002192 6/1979 European Pat. Off. .
0196185 10/1986 European Pat. Off. .
0206497 12/1986 European Pat. Off. .
0217580 4/1987 European Pat. Off. .
0286425 10/1988 European Pat. Off. .
1970891 9/1988 Monaco .

OTHER PUBLICATIONS

Engels, *Tett. Lett.*, 21, 4339–4342 (1980).
Samukov et al., *Bioorg. Khim.*, 9(1), 52–59 (1982): see English abstract at p. 59.
McCollum, "Viral Hepatitis," in *Viral Infections in Humans*, 2nd Ed., Evans ed., Plenum Publ. Co., 1982, New York, Chapter 12.
Horwitz et al., *J. Org. Chem.*, 31 205–211 (1986).
Krenitsky et al., *Biochemistry*, 20, 3615–3621 (1981).
Davies et al., *Biochim. Biophys. Acta*, 564, 448–455 (1979).
Mitsuya et al., *Proc. Nat. Acad. Sci. USA*, 82, 7096–7100 (1985).
Lohse et al., *Eur. J. Pharmacol.*, 156, 157–160 (1988); see also *Chem. Abstr.*, 110: p. 71, Abstract No. 18631f.
Averett, *J. Virological Methods*, 23, 263–276 (1989).
Prisbe et al., *Synthetic Comm.*, 15(5), 401–409 (1985).
Johnson et al., *Biochem. Biophys. Res. Comm.*, 148(3), 1251–1258 (1987).
Baba et al., *Antimicrobial Agents Chemotherapy*, 31(10), 1613–1617 (1987).
Frank et al., *Antimicrobial Agents Chemotherapy*, 31(9), 1369–1374 (1987).
Balzarini et al., *Molecular Pharmacology*, 32, 162–167 (1987).
Blau et al., *I. Chromatography*, 420, 1–12 (1987).
Doctrow et al., *Biochemical Pharmacology*, 36(14) 2255–2262 (1987).
Herdewijn et al., *J. Med. Chem.*, 30, 2131–2137 (1987).
Olson et al., *Nucleic Acids Research*, 2(1), 43–60 (1975).
Robins et al., *J. Am. Chem. Soc.*, 98(25), 8213–8217 (1976).
Cooney et al., *Biochem. Pharmacology*, 36(11), 1765–1768 (1987).
Dahlberg et al., *Proc. Nat. Acad. Sci. USA*, 84, 2469–2473 (1987).
Stoeckler et al., *Biochemistry*, 19(1), 102–107 (1980).
Carlson et al., *Biochim. Biophys. Acta*, 566(2), 259–265 (1979).
Bass et al., *Biochemistry*, 25(16), 4473–4478 (1986).

*Primary Examiner*—Johnnie R. Brown
*Assistant Examiner*—L. Eric Crane
*Attorney, Agent, or Firm*—Donald Brown; Lawrence A. Nielsen; Hannah O. Green

[57] ABSTRACT

This invention relates to certain 6-substituted 2',3'-dideoxypurine nucleosides and pharmaceutically acceptable derivatives thereof and their use in the treatment of human immunodeficiency virus (HIV) and hepatitis B virus (HBV) infections. Also provided are pharmaceutical formulations and processes for the production of the compounds of the invention.

7 Claims, No Drawings

THERAPEUTIC NUCLEOSIDES

This is a divisional of copending application Ser. No. 07/417,989 filed on Oct. 6, 1989 now U.S. Pat. No. 5,068,320, which is a continuation-in-part of application Ser. No. 179,435, filed Apr. 8, 1988, now abandoned.

FIELD OF THE INVENTION

The present invention relates to 6-substituted 2',3'-dideoxypurine nucleosides, pharmaceutically acceptable derivatives thereof, and their use in therapy, particularly for the treatment of certain viral infections.

BACKGROUND OF THE INVENTION

AIDS is an immunosuppressive or immunodestructive disease that predisposes subjects to fatal opportunistic infections. Characteristically, AIDS is associated with a progressive depletion of T-cells, especially the helper-inducer subset bearing the OKT[4] surface marker.

Human immunodeficiency virus (HIV) has been reproducibly isolated from patients with AIDS or with the symptoms that frequently precede AIDS. HIV is cytopathic and appears to preferentially infect and destroy T-cells bearing the OKT[4] marker, and it is now generally recognized that HIV is the etiological agent of AIDS.

Since the discovery that HIV is the etiological agent of AIDS, numerous proposals have been made for anti-HIV chemotherapeutic agents that may be effective in treating AIDS sufferers. Thus, for example, U.S. Pat. No. 4,724,232 and European Patent Specification No. 196185 describe 3'-azido-3'-deoxythymidine (which has the approved name zidovudine), its pharmaceutically acceptable derivatives and their use in the treatment of human retrovirus infections including AIDS and associated clinical conditions.

European Patent Publication No. 0206497 relates generally to 2',3'-dideoxypurine nucleosides for use in the treatment of HIV infections and related conditions. In particular this publication discloses 2,6-diaminopurine-9-$\beta$-D-2',3'-dideoxyribofuranoside for the treatment of HIV infections.

Another group of viral pathogens of major consequence worldwide are the hepatitis viruses, in particular hepatitis B virus (HBV). Clinical effects of infection with HBV range from headache, fever, malaise, nausea, vomiting, anorexia and abdominal pains. Replication of the virus is usually controlled by the immune response, with a course of recovery lasting weeks or months in humans, but infection may be more severe leading to persistent chronic liver disease. In "Viral Infections of Humans" (Second Edition, Ed., Evans, A. S. (1982) Plenum Publishing Corporation, New York), Chapter 12 describes in detail the etiology of viral hepatitis infections.

SUMMARY OF THE INVENTION

We have now discovered that certain 6-substituted 2',3'-dideoxypurine nucleosides, as referred to below, are useful for the treatment of viral infections, particularly retroviral infections and especially AIDS.

Certain 6-substituted purine nucleosides have previously been described, and in particular 6-methylaminopurine-9-$\beta$-D-2',3'-dideoxyribofuranoside, described hereinafter for its use in the treatment of HIV infections and related conditions, has been disclosed in *Bioorg. Khim.* 9(1) 52-59 (1983).

In a first aspect of the present invention, there are provided novel 6-substituted 2',3'-dideoxynucleosides having the following general formula (I)

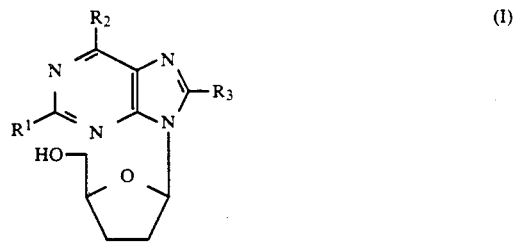

wherein $R_1$ represents hydrogen or amino; and $R_2$ represents halogen (e.g. chlorine), $C_{1-6}$ alkoxy (e.g. propyloxy or isopropoxy), optionally substituted for example by $C_{3-6}$ cycloalkyl (e.g. cyclopropylmethoxy); $C_{3-8}$ cycloalkyloxy (e.g. cyclobutyloxy or cyclopentyloxy); aryloxy (e.g. phenyloxy); aralkyl (e.g. benzyl) or aralkyloxy (e.g. benzyloxy) in which the aryl may optionally be substituted with lower alkyl, hydroxyl or halogen; $C_{3-6}$ cycloalkylthio; $C_{1-6}$ alkylthio; arylthio, or aralkylthio in which the aryl may optionally be substituted with lower alkyl, hydroxy, or halogen; or $R_2$ represents a heterocyclic group containing an oxygen atom or one or two nitrogen atoms, and 3-7 carbon atoms with optional double bonds in the ring (e.g. piperidino, pyrrolidino or furfuryl) optionally containing a sulphur and/or oxygen heteroatom and optionally substituted on the ring by one or more lower alkyl, hydroxyl or halogen groups, $C_{3-6}$ cycloalkylthio, aralkylthio in which the aryl may be substituted with lower alkyl, hydroxy or halogen; or $R_2$ represents an imidazolylthio group in which the imidazolyl moiety may be substituted with lower alkyl and/or C-substituted with nitro; or $R_2$ represents an amino group which is mono or di-substituted by $C_{1-6}$ alkyl (e.g. methyl or ethyl), $C_{1-6}$ alkoxy (e.g. methoxy), hydroxy $C_{1-6}$ alkyl (e.g. hydroxyethyl) and/or $C_{3-6}$ cycloalkyl (e.g. cyclopropyl or cyclopentyl), aryl (e.g. phenyl), aralkyl (e.g. benzyl) in which the aryl may optionally be substituted with lower alkyl, hydroxy, or halogen, allyl optionally substituted with mono- or di-alkyl or alkoxy groups (e.g. dimethyl allyl); and $R_3$ represents hydrogen or amino, and pharmaceutically acceptable derivatives thereof other than the compounds of formula (I) in which $R_1$ and $R_3$ represent hydrogen and $R_2$ represents a methoxy, methylthio or methylamino. Examples of substituted amino groups represented by $R_2$ in formula (I) include ethylamino, ethylmethylamino, cyclopropylamino and isopropylamino.

The above references to "lower alkyl" denote groups containing 1 to 6 carbon atoms preferably methyl or ethyl. The references to halogen include chlorine, bromine, iodine and fluorine, chlorine and iodine being particularly preferred.

Preferred classes of the compounds of formula (I) include those in which $R_1$ and $R_3$ represent hydrogen and $R_2$ represents a substituted amino group, for example, a mono-$C_{3-6}$ cycloalkylamino group or a mono- or di- $C_{1-6}$ alkylamino group.

Also preferred are compounds of formula (I) in which $R_3$ represents hydrogen; $R_2$ represents a substituted amino group, for example, a mono-$C_{3-6}$ cycloalkylamino group or a mono- or di-$C_{1-6}$ alkylamino group, or $R_2$ represents a $C_{1-6}$ alkoxy group; and $R_1$ represents hydrogen or amino.

DETAILED DESCRIPTION OF THE INVENTION

The following compounds are preferred compounds of the present invention:

1. 6-N-Piperidinopurine-9-β-D-2',3'-dideoxyribofuranoside
2. 6-Chloropurine-9-β-D-2',3'-dideoxyribofuranoside
3. 6-Ethylaminopurine-9-β-D-2',3'-dideoxyribofuranoside
4. 6-Ethylmethylamino-9-β-D-2',3'-dideoxyribofuranoside
5. 6-Iodopurine-9-β-D-2',3'-dideoxyribofuranoside
6. 6-(Cyclopropylmethylamino)purine-9-β-D-2',3'-dideoxyribofuranoside
7. 6-Isopropylaminopurine-9-β-D-2',3'-dideoxyribofuranoside
8. Thiamiprine-9-β-D-2',3'-dideoxyribofuranoside
9. 2-Amino-6-n-propoxypurine-9-β-D-2',3'-dideoxyribofuranoside
10. 6-Ethylthiopurine-9-β-D-2',3'-dideoxyribofuranoside
11. 2-Amino-6-benzylthiopurine-9-β-D-2',3'-dideoxyribofuranoside
12. 6-Ethoxypurine-9-β-D-2',3'-dideoxyribofuranoside
13. 6-Dimethylaminopurine-9-β-D-2',3'-dideoxyribofuranoside
14. 6-Hydroxyethylaminopurine-9-β-D-2',3'-dideoxyribofuranoside
15. 6-Cyclopropylaminopurine-9-β-D-2',3'-dideoxyribofuranoside
16. 6-Cyclopentylaminopurine-9-β-D-2',3'-dideoxyribofuranoside
17. 2-Amino-6-methoxypurine-9-β-D-2',3'-dideoxyribofuranoside
18. 6-n-Propoxypurine-9-β-D-2',3'-dideoxyribofuranoside
19. 6-n-Butoxypurine-9-β-D-2',3'-dideoxyribofuranoside
20. 6-Cyclopropylmethoxypurine-9-β-D-2',3'-dideoxyribofuranoside
21. 6-Cyclopentyloxypurine-9-β-D-2',3'-dideoxyribofuranoside
22. 6-Cyclohexyloxypurine-9-β-D-2',3'-dideoxyribofuranoside
23. 6-Cyclobutylaminopurine-9-β-D-2',3'-dideoxyribofuranoside
24. 6-Diethylaminopurine-9-β-D-2',3'-dideoxyribofuranoside
25. 6-Pyrrolidinopurine-9-β-D-2',3'-dideoxyribofuranoside
26. 6-Morpholinopurine-9-β-D-2',3'-dideoxyribofuranoside
27. 6-γ,γ-Dimethylallylaminopurine-9-β-D-2',3'-dideoxyribofuranoside
28. 6-Furfurylaminopurine-9-β-D-2',3'-dideoxyribofuranoside
29. 6-Benzylmercaptopurine-9-β-D-2',3'-dideoxyribofuranoside
30. 6-Anilinopurine-9-β-D-2',3'-dideoxyribofuranoside
31. 2-Amino-6-ethoxypurine-9-β-D-2',3'-dideoxyribofuranoside
32. 2,6,8-Triaminopurine-9-β-D-2',3'-dideoxyribofuranoside
33. 2-Amino-6-benzylaminopurine-9-β-D-2',3'-dideoxyribofuranoside
34. 2-Amino-6-cyclopropylaminopurine-9-β-D-2',3'-dideoxyribofuranoside
35. 2-Amino-6-methylaminopurine-9-β-D-2',3'-dideoxyribofuranoside
36. 2-Amino-6-n-propoxypurine-9-β-D-2',3'-dideoxyribofuranoside
37. 6-Benzylaminopurine-9-β-D-2',3'-dideoxyribofuranoside
38. 6-Isopropoxypurine-9-β-D-2',3'-dideoxyribofuranoside
39. 6-Propylaminopurine-9-β-D-2',3'-dideoxyribofuranoside
40. 6-Cyclohexylaminopurine-9-β-D-2',3'-dideoxyribofuranoside
41. 6-Methylaminopurine-9-β-D-2',3'-dideoxyribofuranoside
42. 2-Amino-6-(cyclopropylmethylamino)-9-β-D-2',3'-dideoxyribofuranoside Compounds 1, 6, 13, 15, 16, 25, 36, 41 and 42 above are particularly preferred on account of their surprisingly high anti-HIV activity.

Compounds containing a 2-amino group are particularly preferred, because they have good activity against hepatitis B virus. Of this group, 6-oxo and 6-amino substituted compounds are especially preferred.

The compounds of formula (I) above and their pharmaceutically acceptable derivatives, also including the compound of formula (I) in which $R_1$ is hydrogen and $R_2$ is methylamino, referred to in the above *Bioorg. Khim* reference, are hereinafter referred to as the compounds according to the invention.

In one aspect of the invention there are provided the compounds according to the invention for use in medical therapy particularly for the treatment of retroviral infections.

Examples of retroviral infections which may be treated in accordance with the invention include human retroviral infections such as human immunodeficiency virus (HIV), e.g. HIV-1 or HIV-2 and human T-cell lymphotropic virus (HLTV), e.g. HTLV-I or HTLV-II infections. The compounds according to the invention are especially useful for the treatment of AIDS and related clincial conditions such as AIDS-related complex (ARC), progressive generalized lymphadenopathy (PGL), AIDS-related neurological conditions, such as multiple sclerosis or tropical paraparesis, anti-HIV antibody-positive and HIV-positive conditions, such as thrombocytopenia purpura. The compounds may also be used in the treatment of psoriasis.

The compounds according to the invention have been found to be particularly applicable to the treatment of asymptomatic infections or diseases in humans caused by or associated with human retroviruses.

The compounds according to the present invention may also be used in the treatment of hepatitis B virus infections and associated clinical disorders.

In a further aspect of the present invention there is included:

a) A method for the treatment of retroviral infections which comprises treating the subject with a therapeutically effective amount of a compound according to the invention.

b) Use of a compound according to the invention in the manufacture of a medicament for the treatment of any of the above-mentioned infections or conditions.

By "a pharmaceutically acceptable derivative" is meant any pharmaceutically acceptable salt, ester, or salt of such ester, of a compound according to the invention or any other compound which, upon administration to the recipient, is capable of providing (directly or indirectly) a compound according to the invention, or an antivirally active metabolite or residue thereof.

Preferred esters of the compounds of the invention include carboxylic acid esters in which the non-carbonyl moiety of the ester grouping is selected from straight or branched chain alkyl, e.g. n-propyl, t-butyl, n-butyl, alkoxyalkyl (e.g. methoxymethyl), aralkyl (e.g. benzyl), aryloxyalkyl (e.g. phenoxymethyl), aryl (e.g. phenyl optionally substituted by halogen, $C_{1-4}$ alkyl or $C_{1-4}$ alkoxy); sulphonate esters such as alkyl- or aralkylsulphonyl (e.g. methanesulphonyl); amino acid esters (e.g. L-valyl or L-isoleucyl); and mono-, di-, or tri-phosphate esters.

An especially preferred ester is the 5'-L-valinate of 6-(cyclopropylmethylamino)purine-9-$\beta$-D-2',3'-dideoxyribofuranoside.

With regard to the above-described esters, unless otherwise specified, any alkyl moiety present advantageously contains 1 to 18 carbon atoms, particularly 1 to 4 carbon atoms. Any aryl moiety present in such esters advantageously comprises a phenyl group.

Any reference to any of the above compounds also includes a reference to a pharmaceutically acceptable salt thereof.

Compounds of formula (I) and their pharmaceutically acceptable derivatives which contain an acidic moiety may form base salts, i.e., salts derived from an appropriate base such as alkali metal (e.g., sodium), alkaline earth metal (e.g., magnesium), ammonium and $NX_4^+$ (wherein X is $C_{1-4}$ alkyl). Examples of such moieties are phosphate ester substitutents and certain heterocyclic groups containing hydroxy substituents.

Specific examples of pharmaceutically acceptable derivatives of the compound of formula (I) that may be used in accordance with the present invention include the monosodium salt and the following 5'-esters: monophosphate; disodium monophosphate; diphosphate; triphosphate; acetate; butyrate; 3-methyl-butyrate; octanoate; palmitate; 3-chlorobenzoate; benzoate; 4-methylbenzoate; hydrogen succinate; pivalate; propionate; valerate and mesylate.

The above compounds according to the invention and their pharmaceutically acceptable derivatives may be employed in combination with other therapeutic agents for the treatment of the above infections or conditions. Examples of such further therapeutic agents include agents that are effective for the treatment of HIV infections or associated conditions such as 3'-azido-3'-deoxythymidine (zidovudine), other 2',3'-dideoxynucleosides such as 2',3'-dideoxycytidine, 2',3'-dideoxyadenosine and 2',3'-dideoxyinosine, acyclic nucleosides (e.g. acyclovir), interferons such as $\alpha$-interferon, renal excretion inhibitors such as probenicid, nucleoside transport inhibitors such as dipyridamole, as well as immunomodulators such as interleukin II and granulocyte macrophage colony stimulating factors. The component compounds of such combination therapy may be administered simultaneously, in either separate or combined formulations, or at different times, e.g. sequentially such that a combined effect is achieved.

The compounds according to the invention, also referred to herein as the active ingredient, may be administered for therapy by any suitable route including oral, rectal, nasal, topical (including buccal and sublingual), vaginal and parenteral (including subcutaneous, intramuscular, intravenous, and intradermal). It will be appreciated that the preferred route will vary with the condition and age of the recipient, the nature of the infection and the chosen active ingredient.

In general, a dose will be in the range of 1.0 to 120 mg per kilogram body weight of the recipient per day. More particularly, a suitable dose will be in the range of 3.0 to 120 mg per kilogram body weight of the recipient per day, preferably in the range of 6 to 90 mg per kilogram body weight per day and most preferably in the range 15 to 60 mg per kilogram body weight per day. The desired dose is preferably presented as two, three, four, five, six or more sub-doses administered at appropriate intervals throughout the day. These sub-doses may be administered in unit dosage forms, for example, containing 10 to 1500 mg, preferably 20 to 1000 mg, and most preferably 50 to 700 mg of active ingredient per unit dosage form.

Ideally, the active ingredient should be administered to achieve peak plasma concentrations of the active compound of from about 1 to about 75 $\mu$M, preferably about 2 to 50 $\mu$M, most preferably about 3 to about 30 $\mu$M. This may be achieved, for example, by the intravenous injection of a 0.1 to 5% solution of the active ingredient, optionally in saline, or orally administered as a bolus containing about 1 to about 100 mg/kg of the active ingredient. Desirable blood levels may be maintained by a continuous infusion to provide about 0.01 to about 5.0 mg/kg/hour or by intermittent infusions containing about 0.4 to about 15 mg/kg of the active ingredient.

While it is possible for the active ingredient to be administered alone it is preferable to present it as a pharmaceutical formulation. The formulations of the present invention comprise at least one active ingredient, as defined above, together with one or more acceptable carriers thereof and optionally other therapeutic agents. Each carrier must be "acceptable" in the sense of being compatible with the other ingredients of the formulation and not injurious to the patient. Formulations include those suitable for oral, rectal, nasal, topical (including buccal and sublingual), transdermal, vaginal or parenteral (including subcutaneous, intramuscular, intravenous and intradermal) administration. The formulations may conveniently be presented in unit dosage form and may be prepared by any methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then if necessary shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintegrant (e.g. sodium starch glycollate, cross-linked povidone, cross-linked sodium carboxymethyl cellulose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach. This is particularly advantageous for purine nucleoside derivatives as such compounds are susceptible to acid hydrolysis.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

The compounds according to the invention and their pharmaceutically acceptable derivatives may be be administered in pharmaceutical formulations comprising liposomes. Preferred derivatives for delivery in liposomes include the mono-, di- and triphosphate esters.

Preferred unit dosage formulations are those containing a daily dose or unit, daily sub-dose, as herein above recited, or an appropriate fraction thereof, of an active ingredient.

The compounds according to the invention may also be presented for use in the form of veterinary formulations, which may be prepared, for example, by methods that are conventional in the art.

It should be understood that in addition to the ingredients particularly mentioned above the formulations of this invention may include other agents conventional in the art having regard to the type of formulation in question, for example, those suitable for oral administration may include such further agents as sweeteners, thickeners and flavoring agents.

The present invention further includes a process for the preparation of a compound according to the invention and pharmaceutically acceptable derivatives thereof which comprises either:

(A) reacting a compound of formula:

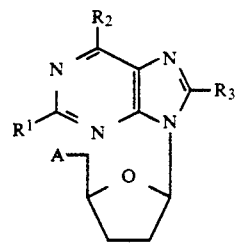

(II)

(wherein $R_1$, $R_2$ and $R_3$ are as hereinbefore defined and A represents a precursor group for the hydroxy group, or for a pharmaceutically acceptable derivative group thereof) with an agent or under conditions serving to convert the said precursor group into the corresponding desired group; or (B) reacting a purine base of formula

B—H    (III)

(wherein B is the required purine moiety of a compound according to the invention)
or a functional equivalent thereof, with a compound serving to introduce the desired 2',3-dideoxyribofuranosyl ring at the 9-position of the purine base of formula (III); and thereafter, or simultaneously therewith, effecting one or more of the following optional conversions:

(i) when a compound of formula (I) is formed, converting it into a pharmaceutically acceptable derivative thereof, (ii) when a pharmaceutically acceptable derivative of a compound of formula (I) is formed, converting the said derivative into a compound of formula (I), or a different derivative thereof.

In the above-described process according to the invention, it will be appreciated that the precursor compounds of formula (I) as well as the above-mentioned agents and conditions, will be selected from those that are known in the art of nucleoside synthetic chemistry. Examples of such conversion procedures are described hereinafter for guidance and it will be understood that they can be modified in conventional manner depending on the desired compound of formula (I). In particular, where a conversion is described which would otherwise result in the undesired reaction of labile groups then such groups may be protected in conventional manner, with subsequent removal of the protecting groups after completion of the conversion.

With regard to process (A), A may represent a protected hydroxy group, e.g. an ester grouping of the type referred to above in relation to formula (I) particularly acetoxy, or an ether group such as a trialkylsilyloxy group, e.g. t-butyldimethylsilyloxy or an aralkoxy group, e.g. triphenylmethoxy. Such groups may be converted for example by hydrolysis to the desired hydroxy group or, by transesterification, to an alternative ester group.

With regard to process (B), this may be effected for excample by treating an appropriate purine base of formula (III) or a salt or protected derivative thereof, with 3'-deoxythymidine for example in the presence of the appropriate pentosyl transferring enzyme.

A compound of formula (I) may be converted into a pharmaceutically acceptable phosphate or other ester by reaction with respectively a phosphorylating agent, e.g. $POCl_3$ or an appropriate esterifying agent, e.g. an acid halide or anhydride. The compound of formula (I), including esters thereof, may be converted into pharmaceutically acceptable salts thereof in conventional manner, e.g. by treatment with an appropriate base. An ester or salt of a compound of formula (I) may be converted into the parent compound, e.g. by hydrolysis.

The following Examples are intended for illustration only and are not intended to limit the scope of the invention in any way. The term "active ingredient" as used in the Examples means a compound of formula (I) or a pharmaceutically acceptable derivative thereof.

EXAMPLE 1

6-N-Piperidinopurine-9-β-D-2',3'-dideoxyribofuranoside

6-N-Piperidinopurine (2.41 mmol, 0.5 g, Sigma Chemicals, St. Louis, Mo.) was dissolved in 10 mL of dimethylsulfoxide with heat. After cooling to room temperature 3'-deoxythymidine (3.62 mmol, 0.82 g) (Horwitz J. P. et al., *J. Org. Chem.* 31, 205 (1966)) was added along with 30 mL of 10 mM potassium phosphate buffer with pH of 6.8 containing 0.04% potassium azide. Purified thymidine phosphorylase (10,000 I.U.) and purine nucleoside phosphorylase (20,000 I.U.) (Krenitsky T. A. et al., *Biochemistry* 20, 3615, 1981 and U.S. Pat. No. 4,381,444) adsorbed onto 10 mL of DEAE cellulose (Whatman) were added, and the suspension was stirred at 35° C. After 8 hours the reaction was filtered, and the filtrate was applied to a series of coupled columns. The initial column contained AG1 X2 hydroxide resin (2.5×10 cm) while the second column was filled with Amberlite XAD-2 resin (2.5×20 cm). After sample application, the columns were washed with a large volume of water and the product was eluted with methanol. After removal of the solvent and redissolving in chloroform:methanol (9:1, v/v), additional chromatography was performed on a column containing silica gel (5×20 cm). The mobile phase was chloroform:methanol (9:1, v/v). Product containing fractions were combined, redissolved in ethanol, and filtered through a 0.22μ filter. The ethanol was evaporated, and the product was redissolved in water. After lyophilization, the 6-N-piperidinopurine-9-β-D-2',3'-dideoxyribofuranoside (0.265 g) analyzed as a 0.1 hydrate containing 0.3 ethanol.

Anal. Calcd. for $C_{15}H_{21}N_5O_2$ 0.3 $C_2H_6O$: Calcd.: C, 58.74; H, 7.27; N, 21.96. Found: C, 58.86; H, 7.14; N, 21.82.

NMR: δ8.36 (s, 1H, $H_8$), 8.19 (s, 1H, $H_2$), 6.23 (dd, 1H, $H_{1'}$), 5.01 (t, 1H, J=5.54, $OH_{5'}$), 4.12 (m, 3H, $H_{4'}$, $CH_2$), 3.52 (m, 2H, $H_{5'}$), 2.37 (m, 2H, $H_{2'}$), 2.04 (m, 2H, $H_{3'}$), 1.61 (b, 6H, $3CH_2$).

EXAMPLE 2

6-Chloropurine-9-β-D-2',3'-dideoxyribofuranoside

The synthesis of 6-chloropurine-9-β-D-2',3'-dideoxyribofuranoside was performed as described in Example 1 except that the 6-chloropurine (Sigma Chemicals, St. Louis, Mo.) was dissolved in 5 mL each of dimethylformamide and dimethoxyethane. After filtering off the solids, the filtrate was reduced to ~5 mL under vacuum then dissolved in 100 mL water. This material was chromatographed on a 2.5×20 cm column containing XAD-2 resin. After washing this column with 500 mL of water, the product was eluted with methanol. Product containing fractions were combined and 20 mL of dry silica gel added. All solvent was removed under vacuum. The dry silica gel was applied to the top of a silica gel column equilibrated with chloroform:methanol (9:1, v/v). Product containing fractions free of 3'-deoxythymidine were combined, and after removal of the solvent under vacuum, the residue was dissolved in ethanol, filtered, then dissolved in water and lyophilized. This material was further purified by chromatography on a column containing Polygosil $C_{18}$ resin in methanol:water (8:2, v/v). After removal of the solvent in vacuo, the product was dissolved in water and lyophilized yielding 0.199 g of 6-chloropurine-9-β-D-2',3'-dideoxyribofuranoside (mp=100° C.).

Anal. Calcd. for $C_{10}H_{11}ClN_4O_2$: Calcd.: C, 47.16; H, 4.35; N, 22.00; Cl, 13.92. Found: C, 47.10; H, 4.35 N, 21.94; Cl, 13.86.

EXAMPLE 3

6-Ethylaminopurine-9-β-D-2',3'-dideoxyribofuranoside

6-Ethylaminopurine (prepared by nucleophilic displacement of the chlorine group on 6-chloropurine (Sigma Chemicals, St. Louis, Mo.) by the amino group of ethylamine) (2.69 mmol, 0.5 g) and 3'-deoxythymidine (Horwitz J. P. et al., *J. Org. Chem.* 31, 205 (1966)) (3.33 mmol, 0.755 g) were combined along with 50 mL of 10 mM potassium phosphate buffer with a pH of 6.8, containing 0.04% potassium azide. Purified thymidine phosphorylase (400 I.U.) and purine nucleoside phosphorylase (700 I.U.) were added and the suspension was stirred at 37° C. After 48 hours an additional 700 units of purine nucleoside phosphorylase and 400 units of thymidine phosphorylase were added, and the reaction was stirred at 37° C. Five days later the reaction was filtered, and the filtrate was applied to a column containing AG-1 ×2 hydroxide resin (2.5×10 cm). The product was eluted with a water wash and chromatographed on Amberlite XAD-2 resin (2.5×20 cm). After sample application, this column was washed with a large volume of water. The product was eluted with methanol. After removal of the solvent, the product was redissolved in water and acetone then lyophilized yielding 0.299 g of 6-ethylaminopurine-9-62 -D-2',3'-dideoxyribofuranoside that analyzed for 0.2 water and 0.1 acetone (mp= <30° C., $[\alpha]_D^{20°}$ = −29.45° (0.5, DMF)).

Anal. Calcd. for $C_{12}H_{17}N_5O_2 \cdot 0.2H_2O \cdot 0.1C_3H_6O$: Calcd.: C, 54.17; H, 6.63: N, 25.68. Found: C, 54.13; H, 6.69; N, 25.75.

EXAMPLE 4

6-Ethylmethylaminopurine-9-β-D-2',3'-dideoxyribofuranoside

The procedure for the synthesis of 6-ethylmethylaminopurine-9-β-D-2',3'-dideoxyribofuranoside was identical to Example 2. The reaction was filtered and the filtrate applied to a Dowex-1-hydroxide column (2.5×10 cm). The product was eluted with 90% methanol/water (v/v) and chromatographed on Amberlite XAD-2 resin (2.5×20 cm) after removal of the solvent to ~5 mL and redissolving in water (100 mL). After sample application, the column was washed with a large volume of water, and the product was eluted with 95% ethanol/water (v/v). Product containing fractions were combined and 20 mL of dry silica gel added. All solvent was removed under vacuum. The dried silica gel was applied to the top of a silica gel column (4.8×20 cm) equilibrated with chloroform:methanol (98:2, v/v). Product containing fractions were combined and after removal of the solvent under vacuum, were dissolved in ethanol and filtered. After removal of the solvent and redissolving in water, the solution was lyophilized yielding 0.3 g of 6-ethylmethylamino-9-$\beta$-D-2',3'-dideoxyribofuranosylpurine that analyzed for a 0.5 hydrate (mp <30° C.).

Anal. Calcd. for $C_{13}H_{19}N_5O_2 0.05H_2O$: Calcd: C, 56.12; H, 6.92; N, 25.17. Found: C, 56.12; H, 6.94; N, 25.14.

NMR: $\delta 8.36$ (s, 1H, H$_8$), 8.19 (s, 1H, H$_2$), 6.23 (dd, 1H, H$_{1'}$), 5.05 (t, 1H, J=5.58, OH$_{5'}$), 4.09 (m, 1, H, H$_{4'}$), 4.08 (m, 2H, CH$_2$), 3.51 (m, 2H, H$_{5'}$), 3.33 (s, 3H, CH$_3$), 2.41 (m, 2H, H$_{2'}$), 2.03 (m, 2H, H$_{3'}$), 1.14 (t, 3H, J=7.01, CH$_3$).

EXAMPLE 5

6-Iodopurine-9-$\beta$-D-2',3'-dideoxyribofuranoside

6-Iodopurine (0.624 g, 2.54 mmol, Sigma Chemicals, St. Louis, Mo.) and 3'-deoxythymidine (0.71 g, 3.13 mmol) (Horwitz, J. P. et al., *J. Org. Chem.* 31, 205 (1966)) were combined with 700 mL 10 mM potassium phosphate buffer with a pH of 6.8, containing 0.04% potassium azide. Purified thymidine phosphorylase (2,000 I. U. ) and purine nucleoside phosphorylase (7,000 I. U.) (Krenitsky T. A. et al., *Biochemistry* 20, 3615, 1981 and U.S. Pat. No. 4,381,444) were added and the suspension was stirred at 35° C. After 48 hours the reaction was filtered, and the filtrate was dried under vacuum. The resulting residue was dissolved in 95% ethanol/water (v/v), and after adding ~20 mL silica gel, the solvent was removed under vacuum. The dried silica was applied to the top of a silica gel column (2.8×50 cm) and the product eluted with chloroform/methanol (95:5, v/v). Fractions containing only product were combined, and the solvent was removed under vacuum. The residue was redissolved in ethanol and filtered through a 0.22$\mu$ filter. After removing most of the ethanol and adding ~25 mL of water, the material was lyophilized yielding 0.088 g of 6-iodopurine-9-$\beta$-D-2',3'-dideoxyribofuranoside that analyzed as a 0.2 hydrate (mp=151°-153° C..

Anal. Calcd. for $C_{10}H_{11}N_4O_2 0.2H_2O$: Calcd.: C, 35.15; H, 3.46: N, 15.77. Found: C, 35.31; H, 3.31; N, 15.83.

EXAMPLE 6

6-(Cyclopropylmethylamino)purine-9-$\beta$-D-2',3'-dideoxyribofuranoside 6-(Cyclopropylmethylamino)purine was prepared by nucleophilic displacement of the chlorine group on 6-chloropurine (Sigma Chemicals. St. Louis, Mo.) by the amino group on cyclopropylmethylamine (Karl Industries, Aurora, Ohio). 6-(Cyclopropylmethylamino)purine (2.64 mmol, 0.50 g) was dissolved in 5 mL of dimethylformamide with heating. After cooling to room temperature 3'-deoxythymidine (3.98 mmol, 0.90 g) (Horwitz J. P. et al., *J. Org. Chem.* 31, 205 (1966)) was added along with 30 mL of 10 mM potassium phosphate buffer with a pH of 6.8 containing 0.04% potassium azide. Purified thymidine phosphorylase (10,000 I.U.) and purine nucleoside phosphorylase (20,000 I. U.) (Krenitsky T. A. et al., *Biochemistry* 20, 3615, 1981 and U.S. Pat. No. 4,381,4440 absorbed onto 10 mL DEAE cellulose (Whatman) were added, and the suspension was stirred at 35° C. After 8 hours the reaction was filtered, and the filtrate was applied to a series of coupled columns. The initial column contained AG1-X2 resin (OH form), 2.5×10 cm, while the second column contained Amberlite XAD-2 resin, 2.5×20 cm. After sample application, the columns were washed with 500 mL water and the product was eluted with methanol. The product was then flash chromatographed on a silica gel column, 5×20 cm, with a mixture of chloroform:methanol (9:1, v/v). Solvent was removed in vacuo and the product gum was transferred in acetone to a vial. Lyophilization yielded 0.588 g of 6-(cyclopropylmethylamino)-9-((2R,5S)-tetrahydro-5-(hydroxymethyl)-2-furyl)-9$\underline{H}$-purine, that analysed for 0.15 water and 0.15 acetone.

Anal. Calcd. for $C_{14}H_{19}N_5O_2 0.15H_2O 0.15C_3H_6O$: Calcd.: C, 57.71; H, 6.77; N, 23.29. Found: C, 57.73; H, 6.94; N, 23.39.

EXAMPLE 7

6-Isopropylaminopurine-9-$\beta$-D-2',3'-dideoxyribofuranoxide

The synthesis of 6-isopropylaminopurine-9-$\beta$-D-2',3'-dideoxyribofuranoside was performed as described in Example 1 except that 6-isopropylaminopurine (prepared from 6-chloropurine (Sigma Chemicals, St. Louis, Mo.) and isopropylamine) was dissolved in 5 mL each of dimethylformamide and dimethylsulfoxide.

After lyophilization, the 6-isopropylaminopurine-9-$\beta$-D-2',3'-dideoxyribofuranoside (0.502 g) analyzed as 0.2 hydrate (mp=55°-57° C.).

Anal. Calcd. for $C_{13}H_{19}N_5O_2 0.2H_2O$: Calcd.: C, 55.58; H, 6.96; N, 24.93. Found: C, 55.54; H, 6.96; N, 25.01.

EXAMPLE 8

Thiamiprine-9-$\beta$-D-2',3'-dideoxyribofuranoside

Thiamiprine (Burroughs Wellcome Co., Research Triangle Park, N.C.) (0.5 g) was dissolved in 2.5 mL dimethylsulfoxide and 15 mL dimethoxyethane and combined with 3'-deoxythymidine (0.8 g) (Horwitz J. P. et al., *J. Org. Chem.* 31, 205, (1966)) in 30 mL potassium phosphate pH 6.8. Purified thymidine phosphorylase (1600 I.U.) and purine nucleoside phosphorylase (70,000 I.U.) (Krenitsky T. A. et al., *Biochemistry* 20, 3615, 1981 and U.S. Pat. No. 4,381,444) were added and the suspension was stirred at 35° C. After 96 hours the reaction was filtered and the volume reduced in vacuo to a syrup. Water (25 mL) was added and the solution stored overnight at 3° C. The precipitate was collected by filtration, suspended in 5 mL dimethylformamide and filtered. To the filtrate was added 15 mL methanol, and the solution was stored at −20° C. After 5 days the solids were collected by filtration, dissolved in 65% methanol/water (v/v) and chromatographed on a AG-1 X2 hydroxide resin. The product was eluted with 65% methanol/water (v/v). After removal of the solvent in vacuo, the solids were dissolved in 20 mL chloroform/methanol (9:1) and chromatographed on a bed of silica gel (3×50 cm) equilibrated with chloroform/methanol (9:1, v/v). Product containing fractions were combined and the solvent removed under vacuum. The residual silica gel was removed from the product by dissolving in 95% ethanol/water (v/v) and filtering through a 0.22$\mu$ filter. The ethanol was evaporated off and ~200 mL water were added. The resulting suspension was lyophilized yielding 0.056 g, Thiamiprine-9-$\beta$-

D-2',3'-dideoxyribofuranoside that analyzed as a 0.4 hydrate containing 0.7 equivalents of methanol (mp=130° C., partial melting at 110° C.).

Anal. Calcd. for $C_{14}H_{16}SN_8O_4 \cdot 0.4H_2O \cdot 0.7CH_4O$: Calcd.: C, 41.84; H, 4.68; S, 7.60; N, 26.55. Found: C, 41.93; H, 4.43; S, 7.48; N, 26,34.

EXAMPLE 9

2-Amino-6-n-propoxypurine-9-β-D-2',3'-dideoxyribofuranoside

2-Amino-6-n-propoxypurine (prepared by nucleophilic displacement of the chlorine group on 2-amino-6-chloropurine (Aldrich Chemical Co., Milwaukee Wis.) by the alkoxy anion formed between sodium hydride and propanol) (0.21 g) and 3'-deoxythymidine (0.29 g) (Horwitz J. P. et al., *J. Org. Chem.* 31, 205 (1966)) were combined in 100 mL potassium phosphate, pH 6.8, with 0.04% potassium azide. Purified thymidine phosphorylase (1200 I.U.) and purine nucleoside phosphorylase (8400 I.U.) (Krenitsky T. A. et al., *Biochemistry* 20, 3615, 1981 and U.S. Pat. No. 4,381,444) were added and the suspension was stirred at 35° C. After 48 hours the reaction was filtered, and the filtrate was chromatographed on a column containing AG-1 X2 hydroxide resin (2×5 cm). The product was eluted with 90% methanol/water (v/v). The solvent was removed under vacuum, and the residue was dissolved in methanol. 10 mL of dry silica gel were added, and the methanol was removed under vacuum. The dried silica gel was applied to a silica gel column (2.5×30 cm) equilibrated in chloroform/methanol (9:1, v/v). This was also the eluting solvent. Fractions containing only product were combined and the solvent was removed under vacuum. The residual silica gel was removed, and the product was dried as described in Example 8. This yielded 0.132 g of 2-amino-6-n-propoxypurine-9-β-D-2',3'-dideoxyribofuranoside that analyzed as a 0.2 hydrate (mp=70° C.).

Anal. Calcd. for $C_{13}H_{19}N_5O_3 \cdot 0.2H_2O$: Calcd.: C, 52.91; H, 6.56; N, 23.73. Found: C, 52.52; H, 6.62; N, 23.49.

EXAMPLE 10

6-Ethylthiopurine-9-β-D-2',3'-dideoxyribofuranoside

6-Ethylthiopurine (5.5 mmoles, 1 g) obtained from Sigma Chemical Co., St. Louis, Mo. and 3'-deoxythymidine (4.47 mmoles) (Horwitz J. P. et al., *J. Org. Chem.* 31, 205 (1966)) were suspended in 50 mL of a 15 mM potassium phosphate solution with a pH of 7.2. Purified thymidine phosphorylase (7890 I.U.) and purine nucleoside phosphorylase (1980 I.U.) (Krenitsky T. A. et al., *Biochemistry* 20, 3615, 1981 and U.S. Pat. No. 4,381,444) were added and the suspension stirred at 35° C. After 144 hours the reaction was filtered and the filtrate stored at −20° C. After thawing, the filtrate was adjusted to pH 10.7 with ammonium hydroxide and chromatographed on a column containing Dowex-1-formate resin (2.5×8 cm). This column was eluted with 30% n-propanol/water (v/v). Fractions containing product were combined and the solvent removed under vacuum. The residue was dissolved in 30% n-propanol/water (v/v) and chromatographed on a column containing BioRad P-2 (5×90 cm). The product was eluted from the column with 30% n-propanol/water (v/v). Product containing fractions were combined and the solvent removed under vacuum yielding 0.427 g of 6-ethylthiopurine-9-β-D-2',3'-dideoxyribofuranoside that analyzed as a 0.5 hydrate.

Anal. Calcd. for $C_{12}H_{16}SN_4O_2 \cdot 0.5H_2O$: Calcd: C, 49.81; H, 5.92; N, 19.36; S, 11.44. Found: C, 49.63; H, 5.95; N, 19.28; S, 11.06.

NMR data: δ8.71 (s, 1H, H$_8$), 8.67 (s, 1H, H$_2$), 6.33 (t, 1H, H$_1$'), 4.1 (m, 2H, OH, H$_4$'), 3.4–3.6 (m, 2H, 5'CH$_2$,) 1.8–2.4 (m, 4H, 2' and 3'CH$_2$), 1.5'(t, 3H, CH$_3$).

EXAMPLE 11

2-Amino-6-Benzylthiopurine-9-β-D-2',3'-dideoxyribofuranoside

2-Amino-6-benzylthiopurine (1.9 mmoles, 0.5 g) obtained from Sigma Chemical Co., St. Louis, Mo. and 3'-deoxythymidine (2.0 mmoles, 0.543 g) (Horwitz, J. P. et al., *J. Org. Chem.* 31, 205 (1966)) were dissolved in 20 mL of 10 mM potassium phosphate buffer, pH 7, containing 0.04% potassium azide. Purified thymidine phosphorylase (2,000 I.U.) and purine nucleoside phosphorylase (2,900 I.U.) (Krenitsky T. A. et al., *Biochemistry* 20, 3615, 1981 and U.S. Pat. No. 4,381,444) were added and the suspension was stirred at 35° C. After three days, 80 mL of 10 mM potassium phosphate buffer, pH 7, were added. One day later the reaction was filtered. The cake was dissolved in 90% methanol/water (v/v), filtered, and the filtrate was chromatographed on a 2.5×10 cm column containing Dowex-1-hydroxide. The product was eluted from the column with 90% methanol/water (v/v). Product containing fractions were combined and after lyophilization yielded 0.086 g of 2-amino-6-benzylthiopurine-9-β-D-2',3'-dideoxyribofuranoside.

Anal. Calcd. for $C_{17}H_{19}SH_5O_2$: Calcd.: C, 57.13; H, 5.36; N, 19.59; S, 8.97. Found: C, 57.02; H, 5.39; N, 19.51; S, 8.89.

NMR data: δ8.18 (s, 1H, H$_8$), 7.3 (m, 5H, ϕ), 6.6 (b, 2H, NH$_2$), 6.08 (dd, 1H, H$_1$'), 4.93 (b, 1H, 5'OH), 4.45 (b, 2H, CH$_2$), 4.08 (m, 1H, H$_4$'), 3.43–3.65 (m, 2H, 5'CH$_2$), 2.35 (m, 2H, 2'CH$_2$), 2.0 (m, 2H, 3'CH$_2$).

EXAMPLE 12

6-Ethoxypurine-9-β-D-2',3'-dideoxyribofuranoside

6-Ethoxypurine (3.0 mmoles, 0.5 g: Sigma Chemicals Co., St. Louis Mo.) and 3'-deoxythymidine (3.3 mmoles, 0.75 g) (Horwitz, J. P. et al., *J. Org. Chem.* 31, 205, (1966)) were suspended in 25 mL of 10 mM potassium phosphate buffer pH 6.8 and containing 0.04% potassium azide. Purified thymidine phosphorylase (800 I.U.) and purine nucleoside phosphorylase (1,200 I.U.) (Krenitsky T. A. et al., *Biochemistry*, 20 3615, 1981 and U.S. Pat. No. 4,381,444) were added and the suspension was stirred at 35° C. After 24 hours, 85 mL of 10 mM potassium phosphate buffer pH 6.8, were added and the reaction stirred for an additional five days at 35° C. The reaction precipitate was removed by filtration and the filtrate chromatographed on a 2.5×10 cm column containing Dowex-1-hydroxide. The product was eluted with 90% methanol/water (v/v) and the product containing fractions combined. After removing the solvent by vacuum, the material was dissolved in 30% n-propanol/water (v/v) and chromatographed on a 5×90 cm column containing BioRad P-2 resin. Product containing fractions were pooled and after lyophilization yielded 0.225 g of 6-ethoxypurine-9-β-D-2',3'-dideoxyribofuranoside that analyzed as a 0.15 hydrate.

Anal. Calcd. for $C_{12}H_{16}N_4O_3 \cdot 0.15H_2O$: Calcd.: C, 53.98; H, 6.15; N, 20.98. Found: C, 54.05; H, 6.15; N, 20.88.

NMR data: $\delta 8.6$ (s, 1H, $H_8$), 8.5 (s, 1H, $H_2$), 6.3 (dd, 1H, $H_{1'}$), 4.97 (t, 1H, 5'OH), 4.6 (m, 2H, —$CH_2$—), 4.1 (m 1H, $H_{4'}$), 3,53 (m, 2H, 5'$CH_2$), 2.41 (m, 2H, 2'$CH_2$), 2.03 (m, 2H, 3'$CH_2$), 1.4 (t, 3H, $CH_3$).

EXAMPLE 13

6-Dimethylaminopurine-9-β-D-2'3'-dideoxyribofuranoside

6-Dimethylaminopurine (6.13 mmoles, 1 g, Sigma Chemical Co., St. Louis, Mo.) and 3'-deoxythymidine (4.44 mmoles, 1 g) (Horwitz J. P. et al., J. Org. Chem. 31, 205 (1966)) were suspended in 50 mL of a 10 mM potassium phosphate solution pH 7.0 containing 0.04% potassium azide. Purified thymidine phosphorylase (2000 I.U.) and purine nucleoside phosphorylase (3000 I.U.) (Krenitsky T. A. et al., Biochemistry 20, 3615, (1981) and U.S. Pat. No. 4,381,444) were added and the suspension stirred at 35° C. After 120 hours the reaction was filtered and the filtrate chromatographed on a column containing Dowex-1-hydroxide resin (2.5×8 cm) with 90% methanol and water (v/v) as the eluent. Fractions containing product were combined and the solvent removed under vacuum. The residue was dissolved in 25 mL 30% n-propanol/water (v/v) and chromatographed on a column containing BioRad P-2(5×90). The product was eluted with 30% n-propanol/water (v/v). Product containing fractions were combined and the solvent removed under vacuum. The residue was dissolved in 30 mL de-ionized water and chromatographed on a column containing Sephadex G-10 resin (5×90 cm). The eluent was water. Appropriate fractions were combined and after lyophilization yielded 6-dimethylaminopurine-9-β-D-2',3'-dideoxyribofuranoside that analyzed as a 0.3 hydrate (mp=162° C.).

Anal. Calcd. for $C_{12}H_{17}N_5O_2 \cdot 0.3H_2O$: Calcd.: C, 53,64; H, 6.60; N 26.06. Found: C, 53.63; H, 6.63; N, 25.8.

EXAMPLE 14

6-Hydroxyethylaminopurine-9-β-D-2',3'-dideoxyribofuranoside

6-Hydroxyethylaminopurine (2.8 mmoles, 0.5 g, Sigma Chemical Co. St. Louis, Mo.) and 3'-deoxythymidine (3.30 mmoles, 0.76 g) (Horwitz J. P. et al., J. Org. Chem. 31, 205 (1966)) were suspended in 75 mL of a 10 mM potassium phosphate buffer, pH of 6.8 containing 0.04% potassium azide. Purified thymidine phosphorylase (400 I.U.) and purine nucleoside phosphorylase (700 I.U.) (Krenitsky T. A. et al., Biochemistry 20, 3615, 1981 and U.S. Pat. No. 4,381,444) were added and the suspension was stirred at 35° C. After 8 days, 600 I.U. thymidine phosphorylase and 1050 I.U. purine nucleoside phosphorylase were added. After an additional day, the reaction was filtered and the filtrate was applied to a 2.5×10 cm column containing Dowex-1-hydroxide. The product was eluted with methanol. Product containing fractions were combined and evaporated under vacuum. The residue was then applied and eluted from a 2.5×50 cm silica gel column under pressure with a mixture of (8:2) chloroform: methanol. Product containing fractions were combined and after lyophilization yielded 6-hydroxyethylaminopurine-9-β-D-2',3'-dideoxyribofuranoside that analyzed as a 0.65 hydrate (mp=153° C.).

Anal Calcd. for $C_{12}H_{17}N_5O_3 \cdot 0.65H_2O$: Calcd.: C, 49.53; H, 6.34; N, 24.07. Found: C, 49.85; H, 6.07; N, 23.70.

EXAMPLE 15

6-Cyclopropylaminopurine-9-β-D-2',3'-dideoxyribofuranoside

6-Cyclopropylaminopurine (prepared from 6-chloropurine (Sigma Chemicals, St. Louis, Mo.) and cyclopropylamine) (2.86 mmoles, 0.5 g) and 3'-deoxythymidine (4.30 mmoles, 1 g) (Horwitz J. P. et al., J. Org. Chem. 31, 205 (1966)) were dissolved in 10 mL of a 1:1 dimethylsulfoxide:N',N'-dimethylformamide mixture and further diluted with 30 mL of a 10 mM potassium phosphate buffer pH 6.8 containing 0.04% potassium azide. Purified thymidine phosphorylase (10,000 I.U.) and purine nucleoside phosphorylase (20,000 I.U.) (Krenitsky T. A. et al., Biochemistry 20, 3615, 1981 and U.S. Pat. No. 4,381,444) absorbed onto 10 mL of DEAE resin (Whatman) were added and the suspension was stirred at 35° C. After 8 hours the reaction was filtered and the filtrate was applied to a series of coupled columns. The initial column contained Dowex-1-hydroxide (2.5×10 cm) while the second column was filled with Amberlite XAD-2 resin (2.5×20 cm). After sample application, the columns were washed with a large volume of water and the product was eluted with methanol. Product containing fractions were combined and after lyophilization yielded 0.54 g of 6-cyclopropylaminopurine-9-β-D-2',3'-dideoxyribofuranoside that analyzed as a 0.55 hydrate (mp=63°-65° C.).

Anal. Calcd. for $C_{13}H_{17}N_5O_2 \cdot 0.55H_2O$: Calcd.: C, 54.75; H, 6,40; N, 24.55. Found: C, 54.67; H, 6.43; N, 24.57.

EXAMPLE 16

6-Cyclopentylaminopurine-β-D-2',3'-dideoxyribofuranoside

6-Cyclopentylaminopurine (prepared from 6-chloropurine (Sigma Chemicals, St. Louis, Mo.) and cyclopentylamine) (2.49 mmoles, 0.506 g) was dissolved in 5 mL N,N-dimethylformamide and 5 mL dimethylsulfoxide. 3'-deoxythymidine (3.94 mmoles, 0.894 g) (Horwitz, J. P. et al., J. Org. Chem. 31, 205 (1966)) was added along with 30 mL of 10 mM potassium phosphate buffer, pH 6.8 and 0.04% potassium azide. The pH was adjusted to 6.8 with acetic acid. Purified thymidine phosphorylase (10,000 I.U.) and purine nucleoside phosphorylase (20,000 I.U.) (Krenitsky T. A. et al., Biochemistry 20, 3615, 1981 and U.S. Pat. No. 4,381,444) bound to DEAE-cellulose (Whatman) was added to the reaction mixture. The suspension was stirred at 35° C. for 8 hours, filtered, and the filtrate stored overnight at −20° C. Upon thawing, the filtrate was applied to a 2.5×10 cm column containing Dowex-1-hydroxide resin. The product was eluted with water. Product containing fractions were combined and chromatographed on a column containing XAD-2 resin (2.5×20 cm). This product was eluted with 350 mL of water followed by methanol. Product containing fractions were combined and the methanol removed under vacuum. The residue was dissolved in water and after lyophilization, yielded 0.459 g of 6-cyclopentylaminopurine-β-D-2',3'-dideoxyribofuranoside that analyzed as a 0.05 hydrate (mp=88° C.).

Anal. Calcd. for $C_{15}H_{21}N_5O_2 0.05H_2O$: Calcd.: C, 59.21 H, 6.99; N, 23.02. Found: C, 59.24; H, 7.05; N, 22.95.

EXAMPLE 17

2-Amino-6-methoxypurine-9-β-D-2',3'-dideoxyribofuranoside

2-Amino-6-methoxypurine (3.0 mmoles, 0.5 g, prepared from 2-amino-6-chloropurine (Aldrich Chemical Co., Milwaukee, Wis.) and methanol) and 3'-deoxythymidine (4.50 mmoles, 1 g) (Horwitz J. P. et al., *J. Org. Chem.* 31, 205 (1966)) were dissolved in 10 mL of a 1:1 dimethylsulfoxide:N',N'-dimethylformamide mixture and further diluted with 30 mL of a 10 mM potassium phosphate buffer with a pH of 6.8 and containing 0.04% potassium azide. Purified thymidine phosphorylase (10,000 I.U.) and purine nucleoside phosphorylase (20,000 I.U.) (Krenitsky et al., *Biochemistry* 20, 3615, 1981 and U.S. Pat. No. 4,381,444) adsorbed onto 10 mL of DEAE resin were added and the suspension was stirred at 35° C. After 8 hours the reaction was filtered and the filtrate was applied to a 2.5×10 cm column containing Dowex-1-hydroxide. Fractions containing product were pooled and reduced to a volume of 70 mL. This sample was applied to a 2.5×20 cm column filled with Amberlite XAD-2 resin. The column was washed with a large volume of water and the product was eluted with methanol. Product containing fractions were combined and after lyophilization yielded 2-amino-6-methoxypurine-9-β-D-2',3'-dideoxyribofuranoside.

Anal. Calcd. for $C_{11}H_{15}N_5O_3$: Calcd.: C, 49.81; H, 5.70; N, 26.40. Found: C, 49.70; H, 5.72; N, 26.34.

EXAMPLE 18

6-n-Propoxypurine-9-β-D-2',3'-dideoxyribofuranoside 6-n-Propoxypurine (0.5 g, 2.8 mmoles, Sigma Chemicals, St. Louis, Mo.) and 3'-deoxythymidine (0.96 g, 4.2 mmoles) (Horwitz, J. P., et al., *J. Org. Chem.* 31, 205 (1966)) were dissolved in 5 mL dimethylsulfoxide and 5 mL N,N-dimethylformamide. 30 mL of 10 mM potassium phosphate buffer, pH 6.8, containing 0.04% potassium azide and purified purine nucleoside phosphorylase (20,000 I.U.) and thymidine phosphorylase (10,000 I.U.) (Krenitsky T. A. et al., *Biochemistry* 20, 3615, 1981 and U.S. Pat. No. 4,381,444) absorbed onto 10 mL of DEAE-cellulose resin were added and the reaction was stirred at 35° C. for 7 hours. The resin was removed by centrifugation and the supernatant applied to a column of AG1-X2 (OH form), 2.5×10 cm, coupled to a column of XAD-2, 2.5×20 cm. The columns were washed with 500 mL of water and the product was eluted with methanol. The product was flash chromatographed on a silica gel column, 3×50 cm, with chloroform:methanol (9:1 v/v). Lyophilization afforded 0.554 g of 6-n-propoxypurine-9-β-D-2',3'-dideoxyribofuranoside that analyzed as a 0.3 hydrate.

Anal. Calcd. for $C_{13}H_{18}N_4O_3 0.3H_2O$: Calcd.: C, 55.04; H, 6.61; N, 19.75. Found: C, 55.05; H, 6.61; N, 19.72.

EXAMPLE 19

6-n-Butoxypurine-9-β-D-2',3'-dideoxyribofuranoside 6-n-Butoxypurine (0.5 g, 2.6 mmoles, Sigma Chemicals, St. Louis, Mo.) and 3'-deoxythymidine (0.70 g, 3.1 mmoles) (Horwitz, J. P. et al., *J. Org. Chem.* 31, 205 (1966)) were suspended in 100 mL of 10 mM potassium phosphate buffer, pH 6.8, containing 0.04% potassium azide. Purified purine nucleoside phosphorylase (3,500 I.U.) and thymidine phosphorylase (800 I.U.) (Krenitsky T. A. et al., *Biochemistry* 20, 3615, 1981 and U.S. Pat. No. 4,381,444) were added and the solution was stirred at 32° C. After 7 days the reaction was filtered and the filtrate applied to a column containing AG1-X2 (OH form), 2.5×10 cm. Product was eluted with 90% aqueous methanol. Solvent was removed in vacuo from the product and the residue was flash chromatographed on a silica gel column, 2.5×80 cm, with chloroform:methanol (8:2, v/v). The product was dissolved in water and applied to a column containing XAD-2, 2.5×20 cm. The column was washed with 500 mL of water and then developed with methanol. Lyophilization yielded 0.276 g of 6-n-butoxypurine-9-β-D-2',3'-dideoxyribofuranoside (mp 55° C.).

Anal. Calcd. for $C_{14}H_{20}N_4O_3$ Calcd.: C, 57.52; H, 6.90; N, 19.17. Found: C, 57.86; H, 7.29; N, 18.83.

EXAMPLE 20

6-Cyclopropylmethoxypurine-9-β-D-2',3'-dideoxyribofuranoside

6-Cyclopropylmethoxypurine was prepared by nucleophilic displacement of the chlorine group on 6-chloropurine (Sigma Chemical Co., St. Louis, Mo.) by the alkoxy anion formed between sodium hydride and cyclopropymethyl alcohol. 6-Cyclopropylmethoxypurine (0.505 g, 26.5 mmoles) and 2',3'-dideoxythymidine (0.908 g, 40.1 mmoles) (Horwitz et al., *J. Org. Chem.* 31, 205 (1966)) were reacted and chromatographed on AG1-X2 (OH form) and XAD-2 as described in Example 18. Product containing fractions were flash chromatographed on a silica gel column, 3×50 cm, with acetonitrile:water (98:2, v/v). Lyophilization yielded 0.496 g of 6-cyclopropylmethoxypurine-9-β-D-2',3'-dideoxyribofuranoside.

Anal. Calcd. for $C_{14}H_{18}N_4O_3$: Calcd.: C, 57.92; H, 6.25; N, 19.30. Found: C, 57.99; H, 6.28; N, 19.27.

EXAMPLE 21

6-Cyclopentyloxypurine-9-β-D-2',3'-dideoxyribofuranoside

6-Cyclopentyloxypurine was prepared by nucleophilic displacement of the chlorine group on 6-chloropurine (Sigma Chemical Co., St. Louis, Mo.) by the alkoxy anion formed between sodium hydride and cyclopentanol.

6-Cyclopentyloxypurine (0.506 g, 2.48 mmoles) and 3'-deoxythymidine (0.856 g, 3.78 mmoles) (Horwitz J. P. et al., *J. Org. Chem* 31, 205 (1966)) were reacted and chromatographed on AG1-X2 (OH form) and XAD-2 as described in Example 18. Solvent was removed in vacuo from product fractions and the residue was flash chromatographed on a silica gel column, 3×50 cm, with chloroform:methanol (95.5, v/v). Lyophilization yielded 0.385 g of 6-cyclopentyloxypurine-9-β-D-2',3'-dideoxyribofuranoside that analyzed as a 0.15 hydrate.

Anal. Calcd. for $C_{15}H_{20}N_4O_3 0.15H_2O$: Calcd.: C, 58.68; H, 6.66; N, 18.25. Found: C, 58.61; H, 6.53; N, 18.25.

EXAMPLE 22

6-Cyclohexyloxypurine-9-β-D-2',3'-dideoxyribofuranoside

6-Cyclohexyloxypurine was prepared by nucleophilic displacement of the chlorine group on 6-chloropurine (Sigma Chemical Co., St. Louis, Mo.) by the alkoxy anion formed between sodium hydride and cyclohexanol. 6-Cyclohexyloxypurine (0.50 g, 2.29 mmoles) and 3'-deoxythymidine (0.776 g, 3.42 mmoles) (Horwitz J. P. et al., *J. Org. Chem.* 31, 205 (1966)) chromatographed on AG1-X2 (OH form) and XAD-2 as described in Example 18 with the exception that 10 mL glyme in addition to the 5 mL dimethyl sulfoxide and 5 mL N,N-dimethylformamide, and a total of 70 mL of 10 mM potassium phosphate buffer, pH 6.8, containing 0.04% potassium azide were used. Lyophilization yielded 0.102 g of 6-cyclohexyloxypurine-9-β-D-2',3'-dideoxyribofuranoside (mp 105° C.) that analyzed as a 0.2 hydrate.

Anal. Calcd. for $C_{16}H_{22}N_4O_3$ 0.2$H_2O$:
Calcd.: C, 59.69; H, 7.01; N, 17.40. Found: C, 59.69; H, 6.93; N, 17.27.

EXAMPLE 23

6-Cyclobutylaminopurine-9-β-D-2',3'-dideoxyribofuranoside

6-Cyclobutylaminopurine was prepared by nucleophilic displacement of the chlorine group on 6-chloropurine (Sigma Chemical Co., St. Louis, Mo.) by the amino group on cyclobutylamine. 6-Cyclobutylaminopurine (0.510 g, 2.62 mmoles) and 3'-deoxythymidine (0.896 g, 3.96 mmoles) (Horwitz J. P. et al., *J. Org. Chem.* 31, 205 (1966)) were reacted and chromatographed on AG1-X2 (OH form) and XAD-2 as described in Example 18. Solvent was removed from product containing fractions and the residue was flash chromatographed on a silica gel column, 3×50 cm, with chloroform:methanol (9:1, v/v). Lyophilization yielded 0.524 g of 6-cyclobutylaminopurine-9-β-D-2',3'-dideoxyribofuranoside (mp 96°–98° C.).

Anal. Calcd. for $C_{14}H_{19}N_5O_2$: Calcd.: C, 58.12; H, 6.62; N, 24.20. Found: C, 58.19; H, 6.65; N, 24.16.

EXAMPLE 24

6-Diethylaminopurine-9-β-D-2',3'-dideoxyribofuranoside

6-Diethylaminopurine was prepared by nucleophilic displacement of the chlorine group on 6-chloropurine (Sigma Chemical Co., St. Louis, Mo.) by the amino group on diethylamine. 6-Diethylaminopurine (0.246 g 1.28 mmoles) and 3'-deoxythymidine (0.463 g, 2.04 mmoles) (Horwitz J. P. et al., *J. Org. Chem.* 31, 205 (1966)) were reacted and chromatographed on AG1-X2 (OH form) and XAD-2 as described in Example 18. Solvent was removed in vacuo from product containing fractions and the residue was flash chromatographed on a silica gel column, 5×20 cm with chloroform:methanol (9:1, v/v). Solvent was removed in vacuo from product containing fractions and the residue was flash chromatographed on a second silica gel column, 2.5×50 cm, with ethyl acetate. The product gum was transferred in acetone to a vial and lyophilization yielded 0.098 g of 6-diethylaminopurine-9-β-D-2',3'-dideoxyribofuranoside that analyzed for 0.25 water and 0.20 acetone.

Anal. Calcd. for $C_{14}H_{21}N_5O_2$ 0.2$C_3H_6O$ 0.25$H_2O$: Calcd.: C, 57.03; H, 7.44; N, 22.78. Found: C, 57.02; H, 7.39; N, 22.72.

EXAMPLE 25

6-Pyrrolidinopurine-9-β-D-2',3'-dideoxyribofuranoside

6-Pyrrolidinopurine was prepared by nucleophilic displacement of the chlorine group on 6-chloropurine by the amino group on pyrrolidine. 6-Pyrrolidinopurine (0.500 g, 2.64 mmoles) and 3-deoxythymidine (0.901 g, 3.98 mmoles) (Horwitz J. P. et al., *J. Org. Chem.* 31, 205 (1966)) were dissolved in 5 mL dimethyl sulfoxide and 5 mL N,N-dimethylformamide. Thirty mL of 10 mM potassium phosphate buffer, pH 6.8 containing 0.04% potassium azide and purified purine nucleoside phosphorylase (20,000 I.U.) and thymidine phosphorylase (10,000 I.U.) (Krenitsky T. A. et al., *Biochemistry* 20, 3615, 1981 and U.S. Pat. No. 4,381,444) adsorbed onto 10 mL of DEAE-cellulose resin were added and the reaction was stirred at 35° C. for 7 hours. The resin was removed by centrifugation and the supernatant applied to a column of AG1-X2 (OH form), 2.5×10 cm, coupled to a column of XAD-2, 2.5×20 cm. The columns were washed with 500 mL of water and the product was eluted with methanol. Lyophilization yielded 0.385 g of 6-pyrrolidinopurine-9-β-D-2',3'-dideoxyribofuranoside that analyzed as a 0.05 hydrate (mp 158°–159° C.).

Anal. Calcd. for $C_{14}H_{19}N_5O_2$ 0.05$H_2O$: Calcd.: C, 57.94; H, 6.63; N, 24.13. Found: C, 57.92; H, 6.67; N, 24.11.

EXAMPLE 26

6-Morpholinopurine-9-β-D-2',3'-dideoxyribofuranoside

6-Morpholinopurine was prepared by nucleophilic displacement of the chlorine group on 6-chloropurine (Sigma Chemical Co., St. Louis, Mo.) by the amino group on morpholine. 6-Morpholinopurine (0.501 g, 2.44 mmoles) and 3'-deoxythymidine (0.842 g, 3.72 mmoles) (Horwitz J. P. et al., *J. Org. Chem.* 31, 205 (1966)) were reacted and chromatographed on AG1-X2 (OH form) and XAD-2 as described in Example 18. Lyophilization yielded 0.292 g of 6-morpholinopurine-9-β-D-2',3'-dideoxyribofuranoside that analyzed as a 0.2 hydrate (mp 97° C.).

Anal. Calcd. for $C_{14}H_{19}N_5O_3$ 0.20$H_2O$: Calcd.: C, 54.43; H, 6.33; N, 22.67. Found: C, 54.48; H, 6.28; N, 22.51.

EXAMPLE 27

6-γ,γ-Dimethylallylaminopurine-9-β-D-2',3'-dideoxyribofuranoside

6-γ,γ-Dimethylallylaminopurine (0.500 g, 2.46 mmoles, Sigma Chemicals, St. Louis, Mo.) and 3'-deoxythymidine (0.752 g, 3.32 mmoles) (Horwitz J. P. et al., *J. Org. Chem.* 31, 205 (1966)) were reacted and chromatographed on AG1-X2 (OH form) as described in Example 18. Solvent was removed in vacuo from product containing fractions and the residue was flash chromatographed on a silica gel column, 3×50 cm, with chloroform:methanol (95:5, v/v). Product containing fractions were then applied to an XAD-2 column, 2.5×20 cm, and eluted with methanol. The product gum was transferred in acetone to a vial and lyophilization yielded 0.445 g of 6-γ,γ-dimethylallylaminopurine- 9-β-D-2',3'-dideoxyribofuranoside that analyzed for 0.45 water and 0.20 acetone.

Anal. Calcd. for $C_{15}H_{21}N_5O_2$ 0.45$H_2O$ 0.2$C_3H_6O$: Calcd.: C, 57.99; H, 7.21; N, 21.68. Found: C, 57.77; H, 6.91; N, 21.41.

EXAMPLE 28

6-Furfurylaminopurine-9-β-D-2',3'-dideoxyribofuranoside

6-Furfurylaminopurine (0.502 g, 2.33 mmoles, Sigma Chemicals, St. Louis, Mo.) and 3'-deoxythymidine (0.754 g, 3.33 mmoles) (Horwitz J. P. et al., *J. Org. Chem.* 31, 205 (1966)) were reacted and chromatographed on AG1-X2 (OH form) and XAD-2 as described in Example 18. Solvent was removed in vacuo from product containing fractions and the residue was flash chromatographed on a silica gel column, 5×50 cm, with chloroform:methanol (9:1, v/v). Lyophilization yielded 0.303 g of 6-furfurylaminopurine-9-β-D-2',3'-dideoxyribofuranoside that analysed as a 0.2 hydrate.

Anal. Calcd. for $C_{15}H_{17}N_5O_3$ 0.2$H_2O$: Calcd.: C, 56.49; H, 5.50; N, 21.96. Found: C, 56.50; H, 5.53; N, 21.97.

EXAMPLE 29

6-Benzylmercaptopurine-9-β-D-2',3'-dideoxyribofuranoside

6-Benzylmercaptopurine (0.501 g, 2.07 mmoles, Sigma Chemicals, St. Louis, Mo.) and 3'deoxythymidine (0.704 g, 3.11 mmoles) (Horwitz J. P. et al., *J. Org. Chem.* 31, 205, (1966)) were reacted and chromatographed on AG1-X2 (OH form) as described in Example 18 except that 10 mL glyme was used to dissolve the purine base. Solvent was removed in vacuo from product containing fractions and the residue was flash chromatographed on a silica gel column, 3×50 cm, with chloroform:methanol (95:5, v/v). The product was transferred in ethanol to a vial and lyophilization yielded 0.304 g of 6-benzylmercapto-purine-9-β-D-2',3'-dideoxyribofuranoside that analyzed for 0.05 water and 0.05 ethanol (mp 81°-83° C.).

Anal. Calcd. for $C_{17}H_{18}N_4O_2S$ 0.05$H_2O$ 0.05$C_2H_6O$: Calcd.: C, 59.43; H, 5.37; N, 16.21; S, 9.28. Found: C, 59.49; H, 5.38; N, 16.32; S, 9.30.

EXAMPLE 30

6-Anilinopurine-9-β-D-2',3'-dideoxyribofuranoside

6-Anilinopurine (0.500 g, 2.37 mmoles, Sigma Chemicals, St. Louis, Mo.) and 3'-deoxythymidine (0.752 g, 3.32 mmoles) (Horwitz J. P. et al., *J. Org. Chem.* 31, 205 (1966)) were reacted and chromatographed on AG1-X2 (OH form) as described in Example 18. Solvent was removed in vacuo from product containing fractions and the residue was flash chromatographed on a silica gel column, 2.5×50 cm, with chloroform:methanol (95:5, v/v). Lyophilization yielded 0.470 g of 6-anilinopurine-9-β-D-2',3'-dideoxyribofuranoside that analyzed as a 0.05 hydrate (mp 170°-172° C.).

Anal. Calcd. for $C_{16}H_{17}N_5O_2$0.05$H_2O$: Calcd.: C, 61.55; H, 5.52; N, 22.43. Found: C, 61.57; H, 5.55; N, 22.43.

EXAMPLE 31

2-Amino-6-ethoxypurine-9-β-D-2',3'-dideoxyribofuranoside

2-Amino-6-ethoxypurine (0.5 g, 2.8 mmoles prepared by nucleophilic displacement of the chlorine group on 2-amino-6-chloropurine, (Aldrich Chemical Co., Milwaukee, Wis.) by the alkoxy anion formed between sodium hydride and ethanol) and 3'-deoxythymidine (0.950 g, 4.19 mmoles) (Horwitz J. P. et al., *J. Org. Chem.* 31, 205 (1966)) were reacted and chromatographed on AG1-X2 (OH form) and XAD-2 as described in Example 18. Solvent was removed in vacuo from product containing fractions and the residue was flash chromatographed on a silica gel column, 5×20 cm, with chloroform:methanol (9:1, v/v). Lyophilization yielded 0.443 g of 2-amino-6-ethoxypurine-9-β-D-2',3'-dideoxyribofuranoside that analyzed as a 0.3 hydrate (mp 150° C., partial melt at 65° C.).

Anal. Calcd. for $C_{12}H_{17}N_5O_3$0.3$H_2O$: Calcd.: C, 50.63; H, 6.23; N, 24.60. Found: C, 50.77; H, 6.21; N, 24.63.

EXAMPLE 32

2,6,8-Triaminopurine-9-β-D-2',3'-dideoxyribofuranoside 2,6,8-Triaminopurine (0.500 g, 3.0 mmoles) (Davies, R., et al., *Biochim. Biophys, Acta.*, 564(3), 448, 1979) and 3'-dideoxythymidine (1.02 g, 4.50 mmoles) (Horwitz J. P. et al., *J. Org. Chem.* 31, 205 (1966)) were reacted and chromatographed on AG1-X2 (OH form) and XAD-2 as described in Example 18. Lyophilization yielded 0.148 g of 2,6,8-triaminopurine-9-β-D-2',3'-dideoxyribofuranoside that analyzed for 0.7 methanol (mp 154° C.).

Anal. calcd. for $C_{10}H_{15}N_7O_2$0.7$CH_4O$: Calcd.: C, 44,76; H, 6.24; N, 34.08. Found: C, 44.51; H, 5.95; N, 33.78.

EXAMPLE 33

2-Amino-6-benzylaminopurine-9-β-D-2',3'-dideoxyribofuranoside

2-Amino-6-benzylaminopurine (0.2 g, 0.8 mmoles prepared by nucleophilic displacement of the chlorine group on 2-amino-6-chloropurine (Aldrich Chemical Co., Milwaukee, Wis.) by benzylamine) and 3'-deoxythymidine (0.282 g, 1.2 mmoles) (Horwitz J. P. et al., *J. Org. Chem.* 31, 205 (1966)) were reacted and chromatographed on AG1-X2 (OH form) and XAD-2 as described in Example 18 except smaller amounts of purine nucleoside phosphorylase (10,000 I.U.) and thymidine phosphorylase (5,000 I.U.) were used. Lyophilization yielded 0.182 g of 2-amino-6-benzylaminopurine-9-β-D-2',3'-dideoxyribofuranoside that analyzed for 0.60 methanol (mp 92°-94° C.).

Anal. Calcd. for $C_{17}H_{20}N_6O_2$0.60$CH_4O$: Calcd.: C, 58.78; H, 6.28; N, 23.37. Found: C, 58.60; H, 6.06; N, 23.48.

EXAMPLE 34

2-Amino-6-cyclopropylaminopurine-9-β-D-2',3'-dideoxyribofuranoside

2-Amino-6-cyclopropylaminopurine (0.495 g, 2.1 mmoles prepared by nucleophilic displacement of the chlorine group on 2-amino-6-chloropurine (Aldrich Chemical Co., Milwaukee, Wis.) by cyclopropylamine)

and 3'-deoxythymidine (0.73 g, 3.2 mmoles) (Horwitz J. P. et al., *J. Org. Chem.* 31, 205 (1966)) were reacted and chromatographed on AG1-X2 (OH form) and XAD-2 as described in Example 18. Lyophilization yielded 0.419 g of 2-amino-6-cyclopropylamino-purine-9-$\beta$-D-2'-dideoxyribofuranoside that analyzed as a 0.3 hydrate (mp 82°–84° C.).

Anal. Calcd. for $C_{13}H_{18}N_6O_2 \cdot 0.3H_2O$: Calcd.: C, 52.80; H, 6.34; N, 28.42. Found: C, 52.83; H, 6.35; N, 28.44.

EXAMPLE 35

2-Amino-6-methylaminopurine-9-$\beta$-D-2',3-dideoxyribofuranoside

2-Amino-6-methylaminopurine (0.5 g, 3.0 mmoles prepared by nucleophilic displacement of the chlorine group on 2-amino-6-chloropurine (Aldrich Chemical Co., Milwaukee, Wis.) by methylamine) and 3'-deoxythymidine (0.893 g, 3.9 mmoles) (Horwitz J. P. et al., *J. Org. Chem.* 31, 205 (1966)) were suspended in 100 mL of 10 mM potassium phosphate buffer, pH 6.8, containing 0.04% potassium azide. Purified purine nucleoside phosphorylase (2,880 I.U.) and thymidine phosphorylase (1.200 I.U.) (Krenitsky, T. A. et al., *Biochemistry* 20, 3615, 1981 and U.S. Pat. No. 4,381,444) were added and the reaction was stirred at 33° C. for 72 hours. The reaction was applied to a column of AG1-X2 (OH form) 2.5×10 cm, and the product eluted with 90% aqueous methanol. Solvent was removed in vacuo and the residue was flash chromatographed on a silica gel column, 2.5×30 cm, with chloroform:methanol (97.3, v/v). Lyophilization yielded 0.3 g, of 2-amino-6-methylaminopurine-9-$\beta$-D-2',3-dideoxyribofuranoside that analyzed as a 0.4 hydrate (m.p. 95° C. partial melt at 75° C.)

Anal. Calcd. for $C_{11}H_{16}N_6O_2 \cdot 0.4H_2O$: Calcd.: C, 48.66; H, 6.24; N, 30.95. Found: C, 48.57; H, 6.27; N, 30.77.

EXAMPLE 36

2-Amino-6-n-propoxypurine-9-$\beta$-D-2',3'-dideoxyribofuranoside

2-Amino-6-n-propoxypurine (0.21 g, 1.1 mmoles prepared by nucleophilic displacement of the chlorine group on 2-amino-6-chlorpurine (Aldrich Chemical Co., Milwaukee, Wis.) by the alkoxy anion formed between sodium hydride and n-propanol) and 3'-deoxythymidine (0.293 g, 1.3 mmoles) (Horwitz J. P. et al., *J. Org. Chem.* 31, 205, (1966)) were suspended in 100 mL of 10 mM potassium phosphate buffer, pH 7.0 containing 0.04% potassium azide. Purified purine nucleoside phosphorylase (2,880 I.U.) and thymidine phosphorylase (1200 I.U.) (Krenitsky T. A. et al., *Biochemistry* 20, 3615, 1981 and U.S. Pat. No. 4,381,444) were added and the reaction was stirred at 33° C. for 48 hours. The reaction was applied to a column of AG1-X2 (OH form) 2.5×5 cm, and eluted with 90% aqueous methanol. Solvent was removed in vacuo and the residue was flash chromatographed on a silica gel column 2.5×30 cm, with chloroform:methanol (9:1 v/v). Lyophilization yielded 0.132 g, of 2-amino-6-n-propoxypurine-9-$\beta$-D-2',3'-dideoxyribofuranoside that analysed as a 0.2 hydrate (m.p. 70° C.)

Anal. Calcd. for $C_{13}H_{19}N_5O_3 \cdot 0.2H_2O$: Calcd.: C, 52.59; H, 6.59; N, 23.59. Found: C, 52.52; H, 6.62; N, 24.49.

EXAMPLE 37

6-Benzylaminopurine-9-$\beta$-D-2',3'-dideoxyribofuranoside

6-Benzylaminopurine (1.0 g, 4.44 mmoles, Sigma Chemicals, St. Louis, Mo.) and 3'-deoxythymidine (1.0 g, 4.4 mmoles) (Horwitz J. P. et al., *J. Org. Chem.* 31, 205, (1966)) were suspended in 50 mL of 15 mM potassium phosphate buffer, pH 7.2. Purified purine nucleoside phosphorylase (2,000 I.U.) and thymidine phosphorylase (7,900 I.U.) (Krenitsky T. A. et al., *Biochemistry* 20, 3615, 1981 and U.S. Pat. No. 4,381,444) were added and the reaction was stirred at 25° C. After 1 hour, 6 mL of diglyme were added and the reaction was stirred at 37° C. for 6 days. The reaction filtrate was adjusted to pH 10.5 with ammonium hydroxide, applied to a column of AG1-X2 (formate form), 2×6 cm, and the product eluted with 30% aqueous propanol. The product was then chromatographed on a P-2 column, 2.5×90 cm, eluted with 30% aqueous propanol and lyophilization yielded 0.063 g of 6-benzylaminopurine-9-$\beta$-D-2',3'-dideoxyribofuranoside that analysed as a 0.5 hydrate (m.p. 65° C.).

Anal. Calcd. for $C_{17}H_{19}N_5O_2 \cdot 0.5H_2O$: Calcd.: C, 61.06; H, 6.03; N, 20.94. Found: C, 61.29; H, 6.21; N, 20.69.

EXAMPLE 38

6-iso-Propoxypurine-9-$\beta$-D-2'-3'-dideoxyribofuranoside 6-iso-Propoxypurine (0.5 g, 2.8 mmoles, Sigma Chemicals, St. Louis, Mo.) and 3'-deoxythmidine (0.95 g, 4.2 mmoles) (Horwitz J. P. et al, *J. Org. Chem.* 31, 205 (1966)) were reacted and chromatographed on AG1-X2 (OH form) and XAD-2 as described in Example 18. Solvent was removed in vacuo from product fractions and the residue was dissolved in 30% aqueous propanol. Chromatography on a G-10 column, 5×90 cm, developed with 30% aqueous propanol yielded a gum which was transferred in acetone to a lyophilisation flask. Lyophilization yielded 0.313 g of 6-iso-propoxypurine-9-$\beta$-D-2',3'-dideoxyribofuranoside that analysed for 0.2 water and 0.2 acetone (m.p. 75° C.).

Anal. Calcd. for $C_{13}H_{18}N_4O_3 \cdot 0.2C_3H_6O0 \cdot 0.2H_2O$: Calcd.: C, 55.65; H, 6.73; N, 19.09. Found: C, 55.65; H, 6.59; N, 19.12.

EXAMPLE 39

6n-Propylaminopurine-9-$\beta$-D-2',3'-dideoxyribofuranoside 6-n-Propylaminopurine (0.500 g, 2.81 mmoles, Sigma Chemicals, St. Louis, Mo.) and 3'-deoxythymidine (0.957 g, 4.26 mmoles) (Horwitz J. P. et al., *J. Org. Chem.* 31, 205 (1966) were reacted and chromatographed on AG1-X2 (OH-form) and XAD-2 as described in Example 18 except than the 5 mL dimethyl sulfoxide was replaced with an additional 5 mL N,N-dimethylformamide. Solvent was removed in vacuo from product containing fractions and the residue was flash chromatographed on a silica gel column, 3×50 cm, with chloroform: methanol (9:1 v/v). Lyophilization yield 0.499 g of 6-n-propylaminopurine-9-$\beta$-D-2',3'-dideoxyribofuranoside that analysed as a 0.7 hydrate.

Anal. Calcd. for $C_{13}H_{19}N_5O_2 \cdot 0.7H_2O$: Calcd.: C, 53.85; H, 7.09; N, 24.15. Found: C, 53.93; H, 7.08; N, 24.18.

EXAMPLE 40

6-Cyclohexylaminopurine-9-$\beta$-D-2',3'-dideoxyribofuranoside

6-Cyclohexylaminopurine was prepared by nucleophilic displacement of the chlorine group of 6-chloropurine by cyclohexylamine.

6-Cyclohexylaminopurine (1.0 g, 5 mmoles) and 3'-deoxythymidine (2.07 g, 9.1 mmoles) (Horwitz J. P. et al., *J. Org. Chem.* 31, 205 (1966)) were dissolved in 25 mL 2-methoxyethyl ether and 500 mL of 10 mM potassium phosphate buffer, pH 7.2. Purified purine nucleoside phosphorylase (5,000 I.U.) and thymidine phosphorylase (3850 I.U.) (Krenitsky T. A. et al., *Biochemistry* 20, 3615, 1981 and U.S. Pat. No. 4,381,444) were added and the reaction was stirred at 37° C. for 7 days. The reaction mixture was applied to a column of XAD-2 and washed extensively with water. Product was eluted with 90% aqueous methanol. UV absorbing fractions were pooled and applied to a column of AG1-X2 (OH form), 2×12 cm, and the product was eluted with 30% aqueous methanol. The product was further chromatographed on a P-2 column, 2.5×90 cm, and a G-10 column, 2.5×90 cm, and each column was eluted with 30% aqueous propanol. Lyophilization yielded 0.093 g of 6-cyclohexylaminopurine-9-$\beta$-D-2',3'-dideoxyribofuranoside (mp 70°-72° C.).

Anal. Calcd. for $C_{16}H_{23}N_5O_2$: Calculated: C, 60.55; H, 7.30; N, 22.07. Found: C, 60.37; H, 7.39; N, 21.94.

EXAMPLE 41

6-Methylaminopurine-9-$\beta$-D-2',3'-dideoxyribofuranoside

6-Methylaminopurine (4.31 mmoles, 1 g) obtained from Sigma Chemical Co., St. Louis, Mo. and 3'-deoxythymidine (4.40 mmoles, 1 g) (Horwitz J. P. et al., *J. Org. Chem.* 31, 205 (1966)) were suspended in 50 mL of 10 mM potassium phosphate buffer, pH 7, and 0.04% potassium azide. Purified thymidine phosphorylase (2,000 I.U.) and purine nucleoside phosphorylase (2,400 I.U.) (Krenitsky T. A. et al., *Biochemistry* 20, 3615, 1981 and U.S. Pat. No. 4,381,444) were added and the suspension was stirred at 35° C. After three days, the reaction was stored at −20° C. Upon thawing, the reaction was filtered and the filtrate applied to a 2.5×10 cm column containing Dowex-1-hydroxide. The product was eluted from the column with 90% methanol/water (v/v). Product containing fractions were combined and the solvent removed under vacuum. This material was chromatographed twice on a 5×90 cm column containing BioRad P-2 resin with 30% n-propanol/water (v/v). Product containing fractions were pooled, and after lyophilization yielded 0.391 g of 6-methylaminopurine-9-$\beta$-D-2',3'-dideoxyribofuranoside that analysed as a 0.1 hydrate.

Anal. Calcd. for $C_{11}H_{15}N_5O_2 \cdot 0.1H_2O$: Calcd.: C, 52.62; H, 6.10; N, 27.89. Found: C, 52.75; H, 6.16; N, 28.01.

NMR data: $\delta 8.34$ (s, 1H, $H_8$), 8.12 (s, 1H, $H_2$), 7.72 (b, 1H, NH) 6.23 (dd, 1H, $H_{1'}$), 5.06 (t, 1H, 5' OH), 4.10 (m, 1H, $H_{4'}$) 3.58-3.69 (m, 1H 5' $CH_2$), 3.45-3.55 (m, 1H, 5' $CH_2$), 2.95 (b, 3H, $CH_3$), 2.40 (m, 2H, 2'$CH_2$) and 2.07 (m, 2H, 3' $CH_2$).

EXAMPLE 42

2-Amino-6-(cyclopropylmethylamino)-9-$\beta$-D-2',3'-dideoxyribofuranoside 6-(Cyclopropylmethylamino)purine (0.022 moles, 0.5 g) and 3'-deoxythymidine (0.0032 moles, 0.73 g) were suspended in 10 mL dimethylformamide/dimethylsulfoxide (1:1) and 50 mL of 10 mM potassium phosphate buffer, pH of 6.8 that contained 0.04% potassium azide. Immobilized thymidine phosphorylase and purine nucleoside phosphorylase (10.7 mL) were added and the suspension mixed on a shaker bath at 37° C. The reaction was monitored by TLC (Silica gel $CHCl_3$:MeOH (9:1). After 24 hours the solids were filtered off and discarded and the filtrate diluted to 300 mL with water. Chromatography was performed by coupling a column containing AG1-X2 hydroxide resin (2.5×7 cm) to a column containing XAD-2 resin (2.5×11 cm). After sample application the resins were washed with 1 L of water. Product was eluted with 90% methanol/water (v/v). Further chromatography was performed on a silica gel column (5×30 cm). The mobile phase was chloroform/methanol (98:2, v/v). Product containing fractions were combined and after lyophilization yielded 0.17 g that analyzed as a gum containing 0.9 equivalents water (24%): mp<25° C.; TLC $R_f$ 0.83 (silica gel, $CHCl_3$:$CH_3OH$/9:1); $[\alpha]_D^{20°} = -27.2°$ (c=0.5, DMF); UV $\lambda_{max}$ ($\epsilon \times 10^{-3}$) at pH 7, 287 nm (22.5), 263 nm (13.9); at pH 13,287 nm (21.3), 263 nm (13.1).

Anal. Calcd. for $C_{14}H_{20}N_6O_2 \cdot 0.9H_2O$: Calcd.: C, 52.46; H, 6.85; N, 26.22. Found: C, 52.60; H, 6.75; N, 26.15.

NMR data: $^1$H-NMR (200 MHz, DMSO-$d_6$): $\delta 7.95$ (s, 1H, $H_8$), 6.05 (m, 1H, $H_{1'}$), 5.79 (b, 2H, $NH_2$), 4.99 (t, 1H, J=5.57 Hz, 5' OH), 4.04 (m, 1H, $H_{4'}$), 3.53 (m, 2H, 5' $CH_2$), 3.23 (s, 3H, $CH_3$), 3.21 (m, 1H, CH), 2.3 (m, 2H, 2' $CH_2$), 2.0 (m, 2H, 3' $CH_2$), and 0.80 and 0.65 (2 multiplets, 2H and 2H, 2—$CH_2$—).

EXAMPLE 43

6-(Cyclopropylmethylamino)-9-[(2R,5S)-tetrahydro-5-((pivaloyloxy)methyl)-2-furyl]-9$\underline{H}$-purine The compound of Example 6, 6-(Cyclopropylmethylamino)-9-[(2R,5S)-tetrahydro-5-(hydroxymethyl)-2-furyl]-9H-purine, (0.322 g, 1.1 mmoles) was dissolved in 50 mL acetonitrile. 4-Dimethylaminopyridine (10.5 mg, 0.1 mmoles, Aldrich Chemical Co., Madison, Wis.) and triethylamine (620 μl, 4.4 mmoles, Aldrich Chemical Co., Madison, Wis.) were added and the flask was chilled in an ice bath. Pivalic anhydride (450 μl, 2.2 mmoles, Aldrich Chemical Co., Madison, Wis.) was dissolved in 10 mL acetonitrile and added dropwise to the flask over a period of 15 minutes. The reaction was stirred at room temperature for 24 hours. Additional aliquots of triethylamine (620 μl, 4.4 mmoles) and pivaloyl chloride (250 μl, 2.0 mmoles, Aldrich Chemical Co., Madison, Wis.) were added at 24 hours, 48 hours, 72 hours, and 96 hours. After 120 hours of stirring at room temperature, additional pivaloyl chloride (500 μl, 4 mmoles) and triethylamine (1.24 mL, 8.8 mmoles) were added and the reaction was brought to reflux for 16 hours. The reaction was quenched with methanol and solvents were removed in vacuo. The residue was suspended in 25 mL ethyl acetate and salts were removed by filtration. Solvent was removed in vacuo and the remaining material was chromatographed on a Chromatotron 2 mm silica gel plate with a hexane:acetone mixture (7:3). The product containing fraction was further purified by elution from a silica gel column (2.5×40 cm) with dichloromethane:methanol (98:2). Lyophilization afforded 0.218 g of 6-(cyclopropylmethylamino)-9-[(2R,5S)-tetrahydro-5-((pivaloyloxy)methyl]-2-furyl]-9H-purine as an oil (52% yield).

Anal. Calcd. for $C_{19}H_{27}N_5O_3 \cdot 0.25H_2O$: Calcd.: C, 60.38; H, 7.33; N, 18.53. Found: C, 60.49; H, 7.33; N, 18.38.

NMR data: $^1H$ NMR (200 MHz, DMSO-$d_6$) $\delta$ 8.26 (apparent singlet, 2H, $H_2$ and $H_8$), 6.25 (m, 1H, $H_{1'}$), 4.25 (b, 1H, $H_{4'}$), 4.16 (m, 2H, $H_{5'}$ and $H_{5''}$), 3.36 (s, 3H, N—CH$_3$), 3.21 (b, 1H, N—CHCH$_2$CH$_2$), 2.48 (b, 2H, $H_{3'}$ and $H_{3''}$), 2.11 (m, 2H, $H_{2'}$ and $H_{2''}$), 1.08 (s, 9H, C(CH$_3$)$_3$), 0.84 and 0.70 (2 m, 2H each, N—CHCH$_2$CH$_2$).

EXAMPLE 44

9-((2R,5S)-5-(Acetoxymethyl)-tetrahydro-2-furyl)-6-(cyclopropylmethylamino)-9H-purine 6-(Cyclopropylmethylamino)-9-[(2R,5S)-tetrahydro-5-(hydroxymethyl)-2-furyl]-9H-purine (0.290 g, 1 mmoles), 4-dimethylaminopyridine (10.2 mg, 0.1 mmoles, Aldrich Chemical Co., Madison, Wis.), and triethylamine (620 μl, 4.4 mmoles, Aldrich Chemical Co., Madison, Wis.) were dissolved in 50 mL acetonitrile. The flask was chilled in an ice bath and acetyl chloride (150 μl, 2.1 mmoles, Aldrich Chemical Co., Madison, Wis.) was added. The reaction was brought to room temperature and stirred for 4 hours. Additional aliquots of triethylamine (620 μl, 4.4 mmoles) and acetyl chloride (150 μl, 2.1 mmoles) were added and the reaction was stirred overnight. The reaction was quenched with methanol and solvents were evaporated in vacuo. The residue was suspended in 25 mL ethyl acetate and salts were removed by filtration. Solvent was evaporated in vacuo and the remaining material was chromatographed on a Chromatotron (4 mm silica gel plate) with a mixture of hexane:acetone (7:3). Lyophilization afforded 0.174 g of 9-[(2R,5S)-5-(acetoxymethyl)-tetrahydro-2-furyl]-6-(cyclopropylmethylamino)-9H-purine as an oil (51% yield).

Anal. Calcd. for $C_{16}H_{21}N_5O_3 \cdot 0.55H_2O$: Calcd.: C, 56.31; H, 6.53; N, 20.52. Found: C, 56.26; H, 6.50; N, 20.50.

NMR data: $^1H$ NMR (200 MHz, DMSO-$d_6$) $\delta$ 8.31 and 8.29 (2 s, 2H, $H_2$ and $H_8$), 6.29 (m, 1H, $H_{1'}$), 4.32 (b, 1H, $H_{4'}$), 4.16 (m, 2H, $H_{5'}$ and $H_{5''}$), 3.38 (s, 3H, N—CH$_3$), 3.25 (b, 1H, N—CHCH$_2$CH$_2$), 2.5 (b, 2H, $H_{3'}$ and $H_{3''}$), 2.14 (m, 2H, $H_{2'}$ and $H_{2''}$), 1.98 (s, 3H, CH$_3$COO), 0.88 and 0.73 (2 m, 2H each, N—CHCH$_2$CH$_2$)

EXAMPLE 45

6-(Cyclopropylmethylamino)-9-[(2R,5S)-5-[(hexanoyloxy)methyl]-tetrahydro-2-furyl]-9H-purine 6-(Cyclopropylmethylamino)-9-[(2R,5S)-tetrahydro-5-(hydroxymethyl)-2-furyl]-9H-purine (0.503 g, 1.7 mmoles), triethylamine (2.0 mL, 14 mmoles, Aldrich Chemical Co., Madison, Wis.), and 4-dimethylaminopyridine (10 mg, 0.1 mmoles, Aldrich Chemical Co., Madison, Wis.) were dissolved in 50 mL acetonitrile. Hexanoyl chloride (980 μl, 7.0 mmoles, Aldrich Chemical Co., Madison, Wis.) was added and the reaction was stirred at room temperature for 3 hours. The reaction was quenched with methanol and solvents were evaporated in vacuo. The residue was dissolved in 25 mL ethyl acetate and undissolved salts were removed by filtration. After evaporation of the ethyl acetate, the residue was dissolved in methanol and passed over a silica gel column (4.8×13 cm). The product containing fractions were combined, concentrated, and chromatographed on a Chromatotron (4 mm silica gel plate) with a mixture of hexane:acetone (8:2). The product was further purified on the Chromatotron (2 mm silica gel plate) with a mixture of chloroform:acetone (99:1). Lyophilization afforded 0.268 g of 6-(cyclopropylmethylamino)-9-[(2R,5S)-5-[(hexanoyloxy)methyl]-tetrahydro-2-furyl]-9H-purine as an oil (40% yield).

Anal. Calcd. for $C_{20}H_{29}N_5O_3 \cdot 0.10H_2O$: Calcd.: C, 61.71; H, 7.56; N, 17.99. Found: C, 61.81; H, 7.58; N, 17.92.

NMR data: $^1H$ NMR (300 MHz, DMSO-$d_6$) $\delta$ 8.30 and 8.28 (2s, 2H, $H_2$ and $H_8$), 6.28 (m, 1H, J=6.3 Hz, J=4.2 Hz, $H_{1'}$), 4.30 (b, 1H, $H_{4'}$), 4.23 (m, 2H, $H_{5'}$ and $H_{5''}$), 3.38 (s, 3H, N—CH$_3$), 3.24 (m, 1H, N—CHCH$_2$CH$_2$), 2.51 (b, 2H, $H_{3'}$ and $H_{3''}$), 2.22 (m, 2H, $H_{2'}$ and $H_{2''}$), 2.14 (m, 2H, OOCCH$_2$CH$_2$(CH$_2$)$_2$CH$_3$), 1.45 (apparent pentet, 2H, J=7.3 Hz, OOCCH$_2$CH$_2$(CH$_2$)$_2$CH$_3$), 1.20 (m, 4H, OOCCH$_2$CH$_2$(CH$_2$)$_2$CH$_3$), 0.88 and 0.73 (2m, 2H each, N—CHCH$_2$CH$_2$), and 0.82 (t, 3H, J=6.8 Hz, OOCCH$_2$CH$_2$(CH$_2$)$_2$CH$_3$).

EXAMPLE 46

6-(Cyclopropylmethylamino)-9-((2R,5S)-5-((nonanoyloxy)methyl)-tetrahydro-2-furyl)-9H-purine 6-(Cyclopropylmethylamino)-9-[(2R,5S)-tetrahydro-5-(hydroxymethyl)-2-furyl]-9H-purine (0.498 g, 1.7 mmoles), 4-dimethylaminopyridine (10 mg, 0.1 mmoles, Aldrich Chemical Co., Madison, Wis.), and triethylamine (2.0 mL, 14 mmoles, Aldrich Chemical Co., Madison, Wis.) were dissolved in 50 mL acetonitrile. Nonanoyl chloride (1.26 mL, 7.0 mmoles, Aldrich Chemical Co., Madison, Wis.) was added and the reaction was stirred at room temperature for 3 hours. The reaction was quenched with methanol and solvents were evaporated in vacuo. The residue was dissolved in 25 mL ethyl acetate and undissolved salts were removed by filtration. After evaporation of the ethyl acetate, the residue was dissolved in methanol and passed over a silica gel column (4.8×13 cm). The product containing fractions were combined, concentrated, and chromatographed on a Chromatotron (4 mm silica gel plate) in a mixture of hexane:acetone (80:20). Two separate subsequent runs on the Chromatotron (4 mm silica gel plate) with a mixture of chloroform:acetone (95:5) and a mixture of hexane:acetone (85:15) followed by lyophilization afforded 0.236 g of 6-(cyclopropylmethylamino)-9-((2R,5S)-5-[(nonanoyloxy)methyl]-tetrahydro-2-furyl)-9H-purine as an oil (32% yield).

Anal. Calcd. for $C_{23}H_{35}N_5O_3 \cdot 0.15H_2O$: Calcd.: C, 63.91; H, 8.23; N, 16.20. Found: C, 63.73; H, 8.05; N, 16.05.

NMR data: $^1H$ NMR (300 MHz, DMSO-$d_6$) $\delta$ 8.29 and 8.28 (2s, 2H, $H_2$ and $H_8$), 6.28 (dd, 1H, J=4.5 Hz, J=5.9 Hz, $H_{1'}$), 4.21 (b, 1H, $H_{4'}$), 4.17 (m, 2H, $H_{5'}$ and $H_{5''}$), 3.38 (s, 3H, N—CH$_3$), 3.24 (b, 1H, N—CHCH$_2$CH$_2$), 2.51 (b, 2H, $H_{3'}$ and $H_{3''}$), 2.24 (m, 2H, $H_{2'}$ and $H_{2''}$), 2.16 (m, 2H, OOCCH$_2$CH$_2$(CH$_2$)$_5$CH$_3$), 1.45 (b, 2H, OOCCH$_2$CH$_2$(CH$_2$)—5CH$_3$), 1.22 (b, 10H, OOCCH$_2$CH$_2$(CH$_2$)$_5$CH$_3$), 0.88 and 0.72 (2m, 2H each, N—CHCH$_2$CH$_2$), 0.83 (t, 3H, J=6.7 Hz, OOCCH$_2$C$\underline{H}_2$(CH$_2$)$_5$CH$_3$).

EXAMPLE 47

6-(Cyclopropylmethylamino)-9-((2R,5S)-5-((heptanoyloxy)methyl)-tetrahydro-2-furyl)-9H-purine 6-(Cyclopropylmethylamino)-9-[(2R,5S)-tetrahydro-5-(hydroxymethyl)-2-furyl]-9H-purine (0.310 g, 1.1 mmoles), 4-dimethylaminopyridine (10 mg, 0.1 mmoles, Aldrich Chemical Co., Madison, Wis.), and triethylamine (1.0 mL, 7 mmoles, Aldrich Chemical Co., Madison, Wis.) were dissolved in 50 mL acetonitrile. Heptanoyl chloride (800 μm, 5.0 mmoles, Aldrich Chemical Co., Madison, Wis.) was added and the reaction was stirred at room temperature for 6 hours. The reaction was quenched with methanol and solvents were evaporated in vacuo. The residue was dissolved in acetone and passed over a silica gel column (4.8×13 cm). The product containing fractions were combined, concentrated, and loaded onto preparative silica gel plates (20×20×0.2 cm). The plates were developed in a mixture of chloroform:acetone (80:20). The product was scraped from the preparative plate (R$_f$ 0.5) and eluted from the silica gel with ethanol. After evaporation of the solvent the product was further purified on a Chromatotron (2 mm silica gel plate) with a mixture of hexane:acetone (80:20). Lyophilization afforded 0.227 g of 6-(cyclopropylmethylamino)-9-[(2R,5S)-5-[(heptanoyloxy)methyl]-tetrahydro-2-furyl]-9H-purine as an oil (51% yield).

Anal. Calcd. for C$_{21}$H$_{31}$N$_5$O$_3$.0.10H$_2$O: Calcd.: C, 62.54; H, 7.80; N, 17.36. Found: C, 62.56; H, 7.79; N, 17.28.

NMR data: $^1$H NMR (200 MHz, DMSO-d$_6$) δ8.27 and 8.26 (2s, 2H, H$_2$ and H$_8$), 6.26 (m, 1H, H$_{1'}$), 4.26 (b, 1H, H$_{4'}$), 4.15 (m, 2H, H$_{5'}$ and H$_{5''}$), 3.36 (s, 3H, N—CH$_3$), 3.24 (b, 1H, N—C$\underline{H}$CH$_2$CH$_2$), 2.48 (b, 2H, H$_{3'}$ and H$_{3''}$), 2.17 (m, 4H, H$_{2'}$, H$_{2''}$, OOCC$\underline{H}_2$(CH$_2$)$_4$CH$_3$), 1.42 (b, 2H, OOCC$\underline{H}_2$CH$_2$(CH$_2$)$_2$CH$_3$), 1.19 (b, 6H, OOC(CH$_2$)$_2$(CH$_2$)$_3$CH$_3$), 0.85 and 0.71 (2m, 2H each, N—CHCH$_2$C$\underline{H}_2$), and 0.80 (t, 3H, J=6.9 Hz, OOC(CH$_2$)$_5$C$\underline{H}_3$).

EXAMPLE 48

6-(Cyclopropylmethylamino)-9-((2R,5S)-5-((methoxyacetoxy)methyl)-tetrahydro-2-furyl)-9H-purine 6-(Cyclopropylmethylamino)-9-[(2R,5S)-tetrahydro-5-(hydroxymethyl)-2-furyl]-9H-purine (0.319 g, 1.1 mmoles), 4-dimethylaminopyridine (10 mg, 0.1 mmoles, Aldrich Chemical Co., Madison, Wis.), and triethylamine (1.0 mL, 7 mmoles, Aldrich Chemical Co., Madison, Wis.) were dissolved in 50 mL acetonitrile. Methoxyacetyl chloride (460 μm, 5.0 mmoles, Aldrich Chemical Co., Madison, Wis.) was added and the reaction was stirred at room temperature for 6 hours. The reaction was quenched with methanol and solvents were evaporated in vacuo. The residue was dissolved in acetone and passed over a silica gel column (4.8×13 cm). The UV absorbing eluent was concentrated and separated on a Chromatotron (4 mm silica gel plate) with a mixture of chloroform:acetone (95:5). Solvents were removed in vacuo and the residue was further purified on a preparative silica gel plate (20×20×0.2 cm) developed in a mixture of chloroform:acetone (70:30). The product was scraped from the preparative plate and eluted from the silica gel with ethanol. Lyophilization afforded 0.217 g of 6-(cyclopropylmethylamino)-9-[(2R,5S)-5-[(methoxyacetoxy)methyl]-tetrahydro-2-furyl]-9H-purine as an oil (53% yield).

Anal. Calcd. for C$_{17}$H$_{23}$N$_5$O$_4$.0.45H$_2$O: Calcd.: C, 55.26; H, 6.52; N, 18.95. Found: C, 55.17; H, 6.38; N, 18.84.

NMR data: $^1$H NMR (200 MHz, DMSO-d$_6$) δ8.30 and 8.26 (2s, 2H, H$_2$ and H$_8$), 6.27 (apparent triplet, 1H, H$_{1'}$), 4.31 (b, 1H, H$_{4'}$), 4.21 (b, 2H, H$_{5'}$ and H$_{5''}$), 3.99 (apparent doublet, 2H, OOCCH$_2$OCH$_3$), 3.37 (s, 3H, N—CH$_3$), 3.25 (s, 3H, OOCC$\underline{H}_2$OCH$_3$), 3.19 (b, 1H, N—C$\underline{H}$CH$_2$CH$_2$), 2.46 (b, 2H, H$_{3'}$ and H$_{3''}$), 2.12 (m, 2H, $\underline{H}_{2'}$ and H$_{2''}$), 0.87 and 0.73 (2 m, 2H each, N—CHCH$_2$C$\underline{H}_2$).

EXAMPLE 49

6-(Cyclopropylmethylamino)-9-((2R,5S)-5-((isobutyroyloxy)methyl)-tetrahydro-2-furyl)-9H-purine 6-(Cyclopropylmethylamino)-9-[(2R,5S)-tetrahydro-5-(hydroxymethyl)-2-furyl]-9H-purine (0.321 g, 1.1 mmoles), 4-dimethylaminopyridine (10 mg, 0.1 mmoles, Aldrich Chemical Co., Madison, Wis.), and triethylamine (1.0 mL, 7 mmoles, Aldrich Chemical Co., Madison, Wis.) were dissolved in 50 mL acetonitrile. Isobutyric anhydride (830 μm, 5.0 mmoles, Aldrich Chemical Co., Madison, Wis.) was added and the reaction was stirred at room temperature for 6 hours. The reaction was quenched with methanol and solvents were evaporated in vacuo. The residue was dissolved in acetone and passed over a silica gel column (4.8×13 cm). The product containing fractions were combined, concentrated, and loaded onto preparative silica gel plates (20×20×0.2 cm). The plates were developed in a mixture of chloroform:acetone (80:20). The product was scraped from the preparative plate (R$_f$ 0.5) and eluted from the silica gel with ethanol. After evaporation of the solvent, the product was further purified on a Chromatotron (2 mm silica gel plate) with a mixture of hexane:acetone (80:20). Lyophilization afforded 0.277 g of 6-(cyclopropylmethylamino)-9-((2R,5S)-5-((isobutyroyloxy)methyl)tetrahydro-2-furyl)-9H-purine as an oil (69% yield).

Anal. Calcd. for C$_{18}$H$_{25}$N$_5$O$_3$.0.30H$_2$O: Calcd.: C, 59.26; H, 7.07; N, 19.20. Found: C, 59.30; H, 6.92; N, 19.05.

NMR data: $^1$H NMR (200 MHz, CDCl$_3$) δ8.39 and 7.99 (2 s, 2H, H$_2$ and H$_8$), 6.31 (m, 1H, H$_{1'}$), 4.38 (b, 1H, H$_{4'}$), 4.30 (m, 2H, H$_{5'}$ and H$_{5''}$), 3.46 (s, 3H, N—CH$_3$), 3.22 (b, 1H, N—C$\underline{H}$CH$_2$CH$_2$), 2.56 (b, 3H, H$_{3'}$, H$_{3''}$, and OOC$\underline{H}$(CH$_3$)$_2$), 2.11 (m, 2H, H$_{2'}$ and H$_{2''}$), 1.16 (d, 6H, J=7.0 Hz, OOCH(C$\underline{H}_3$)$_2$), 0.98 and 0.76 (2 m, 2H each, N—CHCH$_2$C$\underline{H}_2$).

EXAMPLE 50

6-(Cyclopropylmethylamino)-9-((2R,5S)-5-((pentanoyloxy)methyl)tetrahydro-2-furyl)-9H-purine 6-(Cyclopropylmethylamino)-9-[(2R,5S)-tetrahydro-5-(hydroxymethyl)-2-furyl]-9H-purine (0.624 g, 2.1 mmoles), 4-dimethylaminopyridine (27 mg, 0.2 mmoles, Aldrich Chemical Co., Madison, Wis.), and triethylamine (2.0 mL, 14 mmoles, Aldrich Chemical Co., Madison, Wis.) were dissolved in 100 mL acetonitrile. Valeryl chloride (1.08 mL, 8.9 mmoles, Aldrich Chemical Co., Madison, Wis.) was added and the reaction was stirred at room temperature for 6 hours. The reaction was quenched with methanol and solvents were evaporated in vacuo. The residue was dissolved in acetone and passed over a silica gel column (4.8×13 cm). After evaporation of the solvent, the product was further purified on a Chromatotron (4 mm silica gel plate) with a mixture of hexane:acetone (85:15). The product containing fractions were combined, concentrated, and loaded onto preparative silica gel plates (20×20×0.2 cm). The plates were developed in a mixture of chloroform-acetone (80:20). The product was scraped from the preparative plate and eluted from the silica gel with ethanol. The product was then flash chromatographed on a silica gel column (2.5×40 cm) with a mixture of chloroform:acetone (95:5). Lyophilization afforded 0.463 g of 6-(cyclopropylmethylamino)-9-((2R,5S)-5-((pentanoyloxy)methyl)-tetrahydro-2-furyl)-9H-purine as an oil (58% yield).

Anal. Calcd.: $C_{19}H_{27}N_5O_3 \cdot 0.25H_2O$: Calcd.: C, 60.38; H, 7.33; N, 18.53. Found: C, 60.66; H, 7.36; N, 18.14.

NMR data: $^1$H NMR (300 MHz, DMSO-$d_6$) δ8.30 and 8.28 (2 s, 2H, $H_2$ and $H_8$), (dd, 1H, J=4.1 Hz, J=6.3 Hz, $H_{1'}$), 4.29 (b, 1H, $H_{4'}$), 4.18 (m, 2H, $H_{5'}$ and $H_{5''}$), 3.38 (s, 3H, N—CH$_3$), 3.25 (b, 1H, N—CHCH$_2$CH$_2$), 2.51 (b, 2H, $H_{3'}$ and $H_{3''}$), 2.22 (m, 2H, OOCCH$_2$CH$_2$CH$_3$), 2.13 (m, 2H, $H_{2'}$ and $H_{2''}$), 1.44 (m, 2H, OOCCH$_2$CH$_2$CH$_2$CH$_3$), 1.23 (m, 2H, OOCCH$_2$CH$_2$CH$_2$CH$_3$), 0.89 and 0.74 (2 m, 2H each, N—CHCH$_2$CH$_2$), and 0.82 (t, 3H, J=7.2 Hz, OOCCH$_2$CH$_2$CH$_2$CH$_3$).

EXAMPLE 51

6-(Cyclopropylmethylamino)-9-((2R,5S)-5-((propanoyloxy)methyl)-tetrahydro-2-furyl)-9H-purine 6-(Cyclopropylmethylamino)-9-[(2R,5S)-tetrahydro-5-(hydroxymethyl)-2-furyl]-9H-purine (0.369 g, 1.3 mmoles), 4-dimethylaminopyridine (10 mg, 0.1 mmoles, Aldrich Chemical Co., Madison, Wis.), and triethylamine (2.0 mL, 14 mmoles, Aldrich Chemical Co., Madison, Wis.) were dissolved in 50 mL acetonitrile. Propionyl chloride (450 μl, 5.2 mmoles, Aldrich Chemical Co., Madison, Wis.) was added and the reaction was stirred at room temperature for 2 hours. The reaction was quenched with methanol and solvents were evaporated in vacuo. Ethyl acetate was added to the residue and undissolved salts were removed by filtration. The filtrate was then applied to a silica gel column (4.8×13 cm) and eluted with methanol. After evaporation of the solvent, the product was eluted to a Chromatotron plate (4 mm silica gel) with a mixture of hexane:acetone (75:25). The product containing fractions were combined, concentrated, and further chromatographed on the Chromatotron (2 mm silica gel plate) with a mixture of chloroform:acetone (95:5). Product containing fractions were applied to preparative silica gel plates (20×20×0.2 cm) which were then developed in chloroform:acetone (85:15). Final purification was achieved by a third run on the Chromatotron (2 mm silica gel plate) with a mixture of hexane:acetone (80:20). Lyophilization afforded 0.178 g of 6-(cyclopropylmethylamino)-9-((2R,5S)-5-((propanoyloxy)methyl)-tetrahydro-2-furyl)-9H-purine as an oil (39% yield).

Anal. Calcd.: $C_{17}H_{23}N_5O_3 \cdot 0.20H_2O$: Calcd.: C, 58.51; H, 6.76; N, 20.07. Found: C, 58.58; H, 6.78; N, 19.90.

$^1$H NMR (200 MHz, DMSO-$d_6$) δ8.28 and 8.26 (2 s, 2H, $H_2$ and $H_8$), 6.26 (m, 1H, $H_{1'}$), 4.28 (b, 1H, $H_{4'}$), 4.14 (m, 2H, $H_{5'}$ and $H_{5''}$), 3.36 (s, 3H, N—CH$_3$), 3.21 (b, 1H, N—CHCH$_2$CH$_2$), 2.48 (b, 2H, $H_{3'}$ and $H_{3''}$), 2.26 (q, 2H, J=7.7 Hz, OOCCH$_2$CH$_3$), 2.18 (m, 2H, $H_{2'}$ and $H_{2''}$), 0.96 (t, 3H, J=7.7 Hz, OOCCH$_2$CH$_3$), 0.84 and 0.70 (2 m, 2H each, N—CHCH$_2$CH$_2$).

EXAMPLE 52

6-(Cyclopropylmethylamino)-9-[(2R,5S)-5-[(p-methylbenzoyloxy)-methyl]-tetrahydro-2-furyl]-9H-purine 6-(Cyclopropylmethylamino)-9-[(2R,5S)-tetrahydro-5-(hydroxymethyl)-2-furyl]-9H-purine (0.295 g, 1.0 mmoles), 4-dimethylaminopyridine (20 mg, 0.2 mmoles, Aldrich Chemical Co., Madison, Wis.), and triethylamine (2.0 mL, 14 mmoles, Aldrich Chemical Co., Madison, Wis.) were dissolved in 50 mL acetonitrile. p-Methylbenzoyl chloride (1.08 mL, 7.0 mmoles, Aldrich Chemical Co., Madison, Wis.) was added and the reaction was stirred at room temperature for 6 hours. The reaction was quenched with methanol and solvents were evaporated in vacuo. The residue was suspended in ethyl acetate and undissolved salts were removed by filtration. The filtrate was concentrated and applied to preparative silica gel plates (20×20×0.2 cm). The plates were developed in a mixture of chloroform:acetone (95:5). The product was scraped from the preparative plate and eluted from the silica gel with ethanol. The product was further purified by flash chromatography on a silica gel column (2.5×40 cm) with a mixture of chloroform:methanol (98:2). Lyophilization afforded 0.330 g of 6-(cyclopropylmethylamino)-9-[(2R,5S)-5-[(p-methylbenzoyloxy)-methyl]-tetrahydro-2-furyl]-9H-purine as an oil (78% yield).

Anal. Calcd.: $C_{22}H_{25}N_5O_3 \cdot 0.020H_2O \cdot 0.30C_2H_6O$; Calcd.: C, 63.89; H, 6.45; N, 16.48. Found: C, 64.10; H, 6.24; N, 16.29.

NMR data: $^1$H NMR (200 MHz, DMSO-$d_6$) δ8.28 and 8.25 (2 s, 2H, $H_2$ and $H_8$), 7.75 and 7.25 (2 m, 2H each, OOCC$_6$H$_4$-CH$_3$), 6.28 (dd, 1H, J=6.5 Hz, J=4.0 Hz, $H_{1'}$), 4.42 (b, 3H, $H_{4'}$, $H_{5'}$ and $H_{5''}$), 3.35 (s, 3H, N—CH$_3$), 3.22 (b, 1H, N—CHCH$_2$CH$_2$), 2.54 (b, 2H, $H_{3'}$ and $H_{3''}$), 2.35 (s, 3H, OOCC$_6$H$_4$—CH$_3$), 2.24 (m, 2H, $H_{2'}$ and $H_{2''}$), 0.85 and 0.70 (2 m, 2H each, N—CHCH$_2$CH$_2$).

EXAMPLE 53

6-(Cyclopropylmethylamino)-9-[(2R,5S)-5-[(benzoyloxy)methyl]-tetrahydro-2-furyl]-9H-purine 6-(Cyclopropylmethylamino)-9[(2R,5S)-tetrahydro-5-(hydroxymethyl)-2-furyl]-9H-purine (0.310 g, 1.1 mmoles), 4-dimethylaminopyridine (27 mg, 0.2 mmoles, Aldrich Chemical Co., Madison, Wis.), and triethylamine (1.1 mL, 8 mmoles, Aldrich Chemical Co., Madison, Wis.) were dissolved in 50 mL acetonitrile. Benzoic anhydride (0.92 g, 4.0 mmoles, Aldrich Chemical Co., Madison, Wis.) was added and the reaction was stirred at room temperature for 6 hours. The reaction was quenched with methanol and solvents were evaporated in vacuo. The residue was suspended in ethyl acetate and undissolved salts were removed by filtration. The filtrate was concentrated and applied to preparative silica gel plates (20×20×0.2 cm). The plates were developed in a mixture of chloroform:acetone (80:20). The product was scraped from the preparative plate and eluted from the silica gel with ethanol. The product was concentrated and then reapplied to preparative silica gel plates (20×20×0.2 cm). These plates were developed in a mixture of dichloromethane:methanol (90:10). The product was scraped from the preparative plate and eluted from the silica gel with ethanol. Final purification of the product was achieved by flash chromatography on a silica gel column (2.5×40 cm) with a mixture of dichloromethane:methanol (90:10). Lyophilization afforded 0.342 g of 6-(cyclopropylmethylamino)-9-[(2R,5S)-5-[(benzoyloxy)-methyl]-tetrahydro-2-furyl]-9H-purine as an oil (78% yield).

Anal. Calcd.: $C_{21}H_{23}N_5O_3.0.03H_2O$: Calcd.: C, 63.24; H, 5.96; N, 17.56. Found: C, 63.23; H, 5.95; N, 17.50.

NMR data: $^1H$ NMR (200 MHz, DMSO-$d_6$) δ8.29 and 8.25 (2 s, 2H, $H_2$ and $H_8$), 7.86, 7.61, and 7.47 (3 m, 5H total, $C_6H_5$), 6.29 (dd, 1H, J=6.5 Hz, J=4.0 Hz, $H_{1'}$), 4.45 (b, 3H, $H_{4'}$, $H_{5'}$ and $H_{5''}$), 3.35 (s, 3H, N—$CH_3$), 3.20 (b, 1H, N—$CHCHCH_2$), 2.52 (b, 2H, $H_{3'}$ and $H_{3''}$), 2.22 (b, 2H, $H_{2'}$ and $H_{2''}$), 0.83 and 0.69 (2 m, 2H each, N—CH$CH_2CH_2$).

EXAMPLE 54

6-(Cyclopropylmethylamino)-9-((2R,5S)-tetrahydro-5-[[(4-nitrobenzoyl)oxy]-methyl-2-furyl]-9H-purine 6-(Cyclopropylmethylaminopurine)-9-](2R,5S)-tetrahydro-5-(hydroxymethyl)-2-furyl]-9H-purine (0.3 g, 0.96 mmoles) was dissolved in 10 mL of acetonitrile. Triethylamine (4.4 mmoles, Aldrich Chemical Co., Madison, WI) and 4-dimethylaminopyridine (0.0102 g, 0.086 mmoles, Aldrich Chemical Co., Madison, WI) in 10 mL of acetonitrile were added and the contents cooled to 0° C. p-Nitrobenzoylchloride (0.27 g, 2 mmoles, Aldrich Chemicals) dissolved in 7 mL acetonitrile was added dropwise maintaining the temperature of the reaction at 0° C. with stirring. After 90 minutes the solvent was removed and the residue dissolved in methanol. After the addition of 25 mL of dry silica gel, the solvent was removed under vacuum and the contents chromatographed on a column containing silica gel (4.8×28 cm). The mobile phase was chloroform:methanol (95:5, v/v). Product containing fractions were combined and further separation performed on a Chromatotron equipped with a 4 mm silica gel plate. The mobile phase was hexane:acetone (7:3, v/v). Product containing fractions were combined and after lyophilization yielded 0.311 g of 6-(cyclopropylmethylamino)-9-[(2R,5S)-tetrahydro-5-[[(4-nitrobenzoyl)oxy]-methyl]-2-furyl]-9H-purine.

Anal. Calcd. for $C_{21}H_{22}N_6O_5$: Calcd.: C, 57.53; H, 5.06; N, 19.17. Found: C, 57.50; H, 5.10; N, 19.22.

NMR data: $^1H$ NMR (200 MHz, DMSO-$d_6$) δ8.05-8.29 (m, 4H, φ), 8.04 and 8.00 (2 s, 2H, $H_2$ and $H_8$), 6.27 (m, 1H, $H_{1'}$), 4.56 (b, 1H, $H_{4'}$), 4.41 (m, 2H, $H_{5'}$ and $H_{5''}$), 3.30 (s, 3H, N—$CH_3$), 3.17 (b, 1H, cyclopropyl CH), 2.6 (b, 2H, $H_{2'}$ and $H_{2''}$), 2.14 (m, 2H, $H_{3'}$ and $H_{3''}$), 0.87 and 0.79 (2 m, 4H, cyclopropyl $CH_2CH_2$).

EXAMPLE 55

6-(Cyclopropylmethylamino)-9-((2R,5S)-tetrahydro-5-(p-aminobenzoylmethyl)-2-furyl)-9H-purine 6-(Cyclopropylmethylamino)-9-[(2R,5S)-tetrahydro-5-(p-nitrobenzoyl)-2-furyl]-9H-purine (0.203 g, 0.463 mmoles) was combined with 10% palladium on activated carbon (0.1 g, Aldrich Chemical Co., Madison, WI) and 4-dimethylaminopyridine (0.0102 g, 0.086 mmoles, Aldrich Chemical Co., Madison, WI) in methanol (150 mL). The reduction was accomplished in an hydrogen atmosphere at 52 psi over 6 hours. After the removal of solids, the filtrate was dried and the residue chromatographed on silica gel with a mobile phase of $CHCL_3/CH_3OH$ (95:5). Product fractions were combined and the after removal of solvent gave 0.127 g of 6-(cyclopropylmethylamino)-9-[(2R,5S)-tetrahydro-5-(p-aminobenzoylmethyl)-2-furyl]-9H-purine that analyzed with 0.5 equivalents of water (66% yield): mp 63° C.; TLC $R_f$ 0.69 (silica gel, $CHCL_3:CH_3OH/9:1$); $[α]_D^{20°} = 6.4°$ (c=0.5, DMF); UV $λ_{max}$ (ε×$10^{-3}$) at pH 7, 275.5 nm (32.2).

Anal. Calcd. for $C_{21}H_{24}N_6O_3.0.5H_2O$: Calcd.: C, 60.42; H, 6.04; N, 20.13. Found: C, 60.54; H, 6.06; N, 20.01.

NMR data: $^1H$ NMR (200 MHz, DMSO-$d_6$) δ8.28, 8.26 (s, 2H, $H_2$ and $H_8$), 7.56 (d, 2H, J=8.6 Hz, $φ_{a,d}$), 6.51 (d, 2H, J=8.6 Hz, $φ_{b,c}$), 6.27 (m, 1H, $H_{1'}$), 5.96 (b, 2H, $NH_2$), 4.32 (m, 3H, $H_{4'}$, $H_{5'}$ and $H_{5''}$), 3.36 (s, 3H, N—$CH_3$), 3.2 (b, 1H, N—$CHCH_2CH_2$), 2.48 (b, 2H, $H_{3'}$ and $H_{3''}$), 2.17 (m, 2H, $H_{2'}$ and $H_{2''}$), 0.86 and 0.71 (2 m, 2H each, N—CH$CH_2CH_2$).

EXAMPLE 56

6-(Cyclopropylmethylamino)-9-[(2R,5S)-tetrahydro-5-[[(acetyl)oxy]-methyl]-2-furyl]-9H-purine 6-(Cyclopropylmethylamino)-9-[(2R,2S)-tetrahydro-5-[hydroxymethyl]-2-furyl]-9H-purine (0.312 g, 1 mmole) was dissolved in 50 ml acetonitrile. Triethylamine (4.4 mmoles) and 4-dimethylaminopyridine (0.1 mmoles) were added and the reaction cooled in an ice bath. Acetyl chloride (2.1 mmoles) was added and the reaction brought to room temperature. After stirring for 4 hours, additional triethylamine (4.4 mmoles) and acetyl chloride (2.1 mmoles) were added. The reaction was stirred overnight at room temperature. Methanol (50 mL) was added and solvent removed in vacuo. The residue was dissolved in ethyl acetate and undissolved salts removed by filtration. The product was separated on a Chromatotron with hexane:acetone/7:3 (4 mm silica gel plate). Lyophilization yielded 0.174 g of 6-(cyclopropylmethylamino)purine-9-[(2R,5S)-tetrahydro-5[[(acetyl)oxy]-methyl]-2-furyl]-9H-purine that analyzed as a 0.55 hydrate.

Anal. Calcd. for $C_{16}H_{21}N_5O_3.0.55H_2O$: Calcd.: C, 56.31; H, 6.53; N, 20.52. Found: C, 56.26; H, 6.50; N, 20.50.

NMR data: $^1H$ NMR (300 MHz, DMSO-$d_6$) δ8.31 and 8.29 (2 s, 2H, $H_2$ and $H_8$), 6.29 (m, 1H, $H_{1'}$), 4.32 (b, 1H, $H_{4'}$), 4.16 (m, 2H, $H_{5'}$ and $H_{5''}$), 3.38 (s, 3H, N—$CH_3$), 3.25 (b, 1H, cyclopropyl CH), 2.5 (b, 2H, $H_{2'}$ and $H_{2''}$), 2.14 (m, 2H, $H_{3'}$ and $H_{3''}$), 1.98 (s, 3H, $CH_3COO$), 0.88 and 0.75 (2 m, 4H, cyclopropyl $CH_2CH_2$).

EXAMPLE 57

6-(Cyclopropylmethylamino)-9-[(2R,5S)-tetrahydro-5-((phenylacetyl)methyl)-2-furyl]9H-purine 6-(Cyclopropylmethylamino)-9-[(2R,5S)-tetrahydro-5-(hydroxymethyl)-2-furyl]-9H-purine (0.5 g, 1.44 mmoles) was dissolved in 20 mL acetonitrile. 4-Dimethylaminopyridine (10.2 mg, 0.08 mmoles) and triethylamine (620 μL, 4.4 mmoles) were added and the flask was chilled in an ice bath under a nitrogen atmosphere. Phenylacetyl chloride (1.11 g, 7.2 mmoles, Aldrich Chemical Co., Madison, WI) was added dropwise to the flask over a period of 15 minutes. The reaction was stirred at room temperature for 0.5 hours. The reaction was quenched with methanol and solvents were removed under vacuo. The residue was dissolved in 2 mL $CHCL_3/CH_3OH$ (9:1) and chromatographed on a column of silica gel (5×15 cm) in the application solvent. Additional chromatography was performed on the product containing fractions using a Chromatotron 2 mm silica gel plate developed with a hexane:acetone mixture (7:3). Lyophilization of the product containing fractions afforded 0.459 g of 6-(cyclopropylmethylamino)-9-[(2R,5S)-tetrahydro-5-[(phenylacetyl)methyl]-2-furyl)]-9H-purine as an oil (78% yield): m.p. <25° C.

Anal. Calcd. for $C_{22}H_{25}N_5O_3$: Calcd.: C, 64.85; H, 6.18; N, 17.19. Found: C, 64.90; H, 6.20; N, 17.10.

NMR data: $^1$H NMR (200 MHz, DMSO-d$_6$) δ8.29, 8.27 (s, 2H, H$_2$ and H$_8$), 7.23 (m, 5H, φ), 6.27 (m, 1H, H$_{1'}$), 4.24 (m, 3H, H$_{4'}$, H$_{5'}$ and H$_{5''}$), 3.61 (d, 2H, Jgem=1.5 Hz, CH$_2$), 3.36 (s, 3H, N—CH$_3$), 3.21 (b, 1H, N—CHCH$_2$CH$_2$), 2.2 (b, 2H, H$_3'$ and H$_3''$), 2.12 (m, 2H, H$_{2'}$ and H$_{2''}$), 0.83 and 0.70 (2 m, 2H, each, N—CHCH$_2$CH$_2$).

EXAMPLE 58

Tablet Formulations

The following formulations A, B and C are prepared by wet granulation of the ingredients with a solution of povidone, followed by addition of magnesium stearate and compression.

| Formulation A | mg/tablet | mg/tablet |
|---|---|---|
| (a) Active ingredient | 250 | 250 |
| (b) Lactose B.P. | 210 | 26 |
| (c) Povidone B.P. | 15 | 9 |
| (d) Sodium Starch Glycollate | 20 | 12 |
| (e) Magnesium Stearate | 5 | 3 |
|  | 500 | 300 |

| Formulation B | mg/tablet | mg/tablet |
|---|---|---|
| (a) Active Ingredient | 250 | 250 |
| (b) Lactose | 150 | — |
| (c) Avicel PH 101 | 60 | 26 |
| (d) Povidone B.P. | 15 | 9 |
| (e) Sodium Starch Glycollate | 20 | 12 |
| (f) Magnesium Stearate | 5 | 3 |
|  | 500 | 300 |

| Formulation C | mg/tablet |
|---|---|
| Active ingredient | 100 |
| Lactose | 200 |
| Starch | 50 |
| Povidone | 5 |
| Magnesium stearate | 4 |
|  | 359 |

The following formulations, D and E, are prepared by direct compression of the admixed ingredients. The lactose in formulation E is of the direct compression type (Dairy Crest-"Zeparox").

| Formulation D | mg/tablet |
|---|---|
| Active ingredient | 250 |
| Pregelatinised Starch NF15 | 150 |
|  | 400 |

| Formulation E | mg/tablet |
|---|---|
| Active ingredient | 250 |
| Lactose | 150 |
| Avicel | 100 |
|  | 500 |

Formulation F (Controlled Release Formulation)

The formulation is prepared by wet granulation of the ingredients (below) with a solution of povidone followed by the addition of magnesium stearate and compression.

|  | mg/tablet |
|---|---|
| (a) Active Ingredient | 500 |
| (b) Hydroxypropylmethylcellulose (Methocel K4M Premium) | 112 |
| (c) Lactose B.P. | 53 |
| (d) Povidone B.P. | 28 |
| (e) Magnesium Stearate | 7 |
|  | 700 |

Drug release takes place over a period of about 6-8 hours and is complete after 12 hours.

EXAMPLE 59

Capsule Formulations

Formulation A

A capsule formulation is prepared by admixing the ingredients of Formulation D in Example 58 above and filling into a two-part hard gelatin capsule. Formulation B (infra) is prepared in a similar manner.

| Formulation B | mg/capsule |
|---|---|
| (a) Active ingredient | 250 |
| (b) Lactose B.P. | 143 |
| (c) Sodium Starch Glycollate | 25 |
| (d) Magnesium Stearate | 2 |
|  | 420 |

| Formulation C | mg/capsule |
|---|---|
| (a) Active ingredient | 250 |
| (b) Macrogol 4000 B.P. | 350 |
|  | 600 |

Capsules of formulation C are prepared by melting the Macrogol 4000 BP, dispersing the active ingredient in the melt and filling the melt into a two-part hard gelatin capsule.

| Formulation D | mg/capsule |
|---|---|
| Active Ingredient | 250 |
| Lecithin | 100 |
| Arachis Oil | 100 |
|  | 450 |

Capsules of formulation D are prepared by dispersing the active ingredient in the lecithin and arachis oil and filling the dispersion into soft, elastic gelatin capsules.

Formulation E (Controlled Release Capsule)

The following controlled release capsule formulation is prepared by extruding ingredients a, b and c using an extruder, followed by spheronisation of the extrudate and drying. The dried pellets are then coated with release-controlling membrane (d) and filled into a two-piece, hard gelatin capsule.

|   | mg/capsule |
|---|---|
| (a) Active ingredient | 250 |
| (b) Microcrystalline Cellulose | 125 |
| (c) Lactose B.P. | 125 |
| (d) Ethyl Cellulose | 13 |
|   | 513 |

EXAMPLE 60

Injectable Formulation

| Formulation A | |
|---|---|
| Active ingredient | 0.200 g |
| Hydrochloric acid solution, 0.1M, or Sodium hydroxide solution, 0.1M q.s. to pH | 4.0 to 7.0 |
| Sterile water q.s. to | 10 mL |

The active ingredient is dissolved in most of the water (35°–40° C.) and the pH adjusted to between 4.0 and 7.0 with the hydrochloric acid or the sodium hydroxide as appropriate. The batch is then made up to volume with the water and filtered through a sterile micropore filter into a sterile 10 mL amber glass vial (type 1) and sealed with sterile closures and overseals.

| Formulation B | |
|---|---|
| Active ingredient | 0.125 g |
| Sterile, Pyrogen-free, pH 7 phosphate buffer, q.s. to | 25 mL |

EXAMPLE 61

| Intramuscular injection | |
|---|---|
| Active ingredient | 0.20 g |
| Benzyl Alcohol | 0.10 g |
| Glycofurol 75 | 1.45 g |
| Water for Injection q.s. to | 3.00 mL |

The active ingredient is dissolved in the glycofurol. The benzyl alcohol is then added and dissolved, and water added to 3 mL. The mixture is then filtered through a sterile micropore filter and sealed in sterile 3 mL amber glass vials (type 1).

EXAMPLE 62

| Syrup | |
|---|---|
| Active ingredient | 0.25 g |
| Sorbitol Solution | 1.50 g |
| Glycerol | 2.00 g |
| Sodium Benzoate | 0.005 g |
| Flavor, Peach 17.42.3169 | 0.0125 mL |
| Purified Water q.s. to | 5.00 mL |

The active ingredient is dissolved in a mixture of the glycerol and most of the purified water. An aqueous solution of the sodium benzoate is then added to the solution, followed by addition of the sorbitol solution and finally the flavor. The volume is made up with purified water and mixed well.

EXAMPLE 63

| Suppository | mg/suppository |
|---|---|
| Active ingredient (63 μm)* | 250 |
| Hard Fat, BP (Witepsol H15 - Dynamit NoBel) | 1770 |
|   | 2020 |

*The active ingredient is used as a powder wherein at least 90% of the particles are of 63 μm diameter or less.

One-fifth of the Witepsol H15 is melted in a steam-jacketed pan at 45° C. maximum. The active ingredient is sifted through a 200 μm sieve and added to the molten base with mixing, using a silverson fitted with a cutting head, until a smooth dispersion is achieved. Maintaining the mixture at 45° C., the remaining Witepsol H15 is added to the suspension and stirred to ensure a homogenous mix. The entire suspension is passed through a 250 μm stainless steel screen and, with continuous stirring, is allowed to cool to 40° C. At a temperature of 38° C.to 40° C., 2.02 g of the mixture is filled into suitable, 2 mL plastic molds. The suppositories are allowed to cool to room temperature.

EXAMPLE 64

| Pessaries | mg/pessary |
|---|---|
| Active ingredient (63 μm) | 250 |
| Anhydrate Dextrose | 380 |
| Potato Starch | 363 |
| Magnesium Stearate | 7 |
|   | 1000 |

The above ingredients are mixed directly and pessaries prepared by direct compression of the resulting mixture.

Antiviral Activity

6-Cyclopropylaminopurine-9-$\beta$-D-2',3'-dideoxyribofuranoside was tested for activity against HIV generally in accordance with the method described by Mitsuya et al., Proc. Nat. Acad. Sci., USA Vol 82, pp 7096–7100, Oct. 1985 and found to have activity against HIV at concentrations of 1 μM.

We claim:

1. The compound 6-N-piperidinopurine-9-$\beta$-D-2',3'-dideoxyribofuranoside or a pharmaceutically acceptable salt thereof.

2. The compound 6-Pyrrolidinopurine-9-$\beta$-D-2',3'-dideoxyribofuranoside or a pharmaceutically acceptable salt thereof.

3. The compound 2-amino-6-(cyclopropylmethylamino)-9-$\beta$-D-2',3'-dideoxyribofuranoside or a pharmaceutically acceptable salt thereof.

4. The compound 2-amino-6-n-propoxypurine-9-$\beta$-D-2',3'-dideoxyribofuranoside or a pharmaceutically acceptable salt thereof.

5. The compound 2-amino-6-benzylthiopurine-9-$\beta$-D-2',3'-dideoxyribofuranoside or a pharmaceutically acceptable salt thereof.

6. The compound 2-amino-6-methoxypurine-9-$\beta$-D-2',3'-dideoxyribofuranoside or a pharmaceutically acceptable salt thereof.

7. The compound 2-amino-6-methylaminopurine-9-$\beta$-D-2',3'-dideoxyribofuranoside or a pharmaceutically acceptable salt thereof.

* * * * *